US007001998B2

(12) United States Patent
McKenzie et al.

(10) Patent No.: US 7,001,998 B2
(45) Date of Patent: Feb. 21, 2006

(54) NUCLEIC ACIDS ENCODING A CHIMERIC GLYCOSYLTRANSFERASE

(75) Inventors: Ian Farquhar Campbell McKenzie, Brunswick (AU); Mauro Sergio Sandrin, Brunswick (AU)

(73) Assignee: The Austin Research Institute (AU)

( * ) Notice: Subject to any disclaimer, the term of this patent is extended or adjusted under 35 U.S.C. 154(b) by 32 days.

(21) Appl. No.: 09/051,034

(22) PCT Filed: Aug. 1, 1997

(86) PCT No.: PCT/AU97/00492

§ 371 (c)(1),
(2), (4) Date: Mar. 31, 1998

(87) PCT Pub. No.: WO98/05768

PCT Pub. Date: Feb. 12, 1998

(65) Prior Publication Data

US 2001/0055584 A1 Dec. 27, 2001

Related U.S. Application Data

(60) Provisional application No. 60/024,279, filed on Aug. 21, 1996.

(30) Foreign Application Priority Data

Aug. 2, 1996 (AU) .............................................. PO1402

(51) Int. Cl.
*C12P 21/04* (2006.01)
*C12N 5/00* (2006.01)
*C07H 21/02* (2006.01)
*C07H 21/04* (2006.01)

(52) U.S. Cl. .................... 536/23.4; 536/23.1; 435/64.7; 435/325

(58) Field of Classification Search .............. 435/320.1, 435/325, 455; 424/93.2, 93.21; 536/23.1, 536/23.4; 514/44

See application file for complete search history.

(56) References Cited

FOREIGN PATENT DOCUMENTS

WO  WO 94/12646   6/1994
WO  WO 94/21799 * 9/1994
WO  WO 95/34202  12/1995

OTHER PUBLICATIONS

Schwientek et al., "Golgi localization and in vivo activity of a mammalian glycosyltransferase (human beta–1,4–galactosyltransferase) in yeast", J. Biol. Chem., 271(7):3398–3405, Feb. 1996.*
Sandrin et al., "Characterization of cDNA clones for porcine alpha(1,3)galactosyltransferase: the enyzme generating the gal–alpha(1,3)gal epitope", Xenotransplantation, 1:81–88, 1994.*

Colley, "Golgi localization of glycosyltransferases: more question than answers", Glycobiology, 7(1):1–13, Feb. 1997.*
Machamer, "Targeting and retention of Golgi membrane proteins", Curr. Opin. Cell Biol., 5(4):606–612, Sep. 1993.*
Gleeson et al., "Targeting of proteins to the Golgi apparatus", Glycoconj. J., 11:381–394, 1994.
Anderson et al., "Human gene therapy", Nature, 392(Supp.):25–30, Apr. 1998.
Verma and Somia, "Gene therapy–promises, problems and prospects", Nature, 389:239–242, Sep. 1997.
Chen, Choa–Guang et al: "Reduction in Gal–alpha– 1, 3–Gal Epitope Expression in Transgenic Mice Expressing Human H– Transferase." XENOTRANSPLANTATION, (1996) vol. 3, No. 1 Part 2, pp. 69.
Cooper D K C et al: "Oligosaccharides and Discordant Xenotransplantation" Immunological Reviews, XX, Munksgaard, vol. 141, Oct. 1, 1994, pp. 31.
Dahdal R Y et al.: "Specific Sequences In The Signal Anchor Of The Beta–Galactoside Alpha– 2, 6– sialytransferase Are Not Essential For Goldi Localization. Membrane Flanking Sequences May Specify Golgi Retention." Journal Of Biological Chemistry, (Dec. 15, 1993) pp. 26310.
Gustafsson K et al: "Alpha1, 3Galactosyltransferase: A Target For In Vivo Genetic Manipulation In Xenotransplantation" Immunological Reviews, XX, Munksgaard, vol. 141, No. 1, Jan. 1, 1994, pp. 59.
Sandrin, M. S. et al.: "Transgenic Approaches For The Reduction In Expression of Galalpha (1,3) Gal For Xenotransplantation." pp. 1.
Sharma A et al.: "Reduction In The Level Of Gal (alpha, 3) Gal in Transgenic Mice and Pigs By The Expression Of An Alpha (1,2) Fucosyltransferase." Proceedings Of The National Academy Of Sciences Of The United State Of America, Jul. 9, 1996, pp. 7190.
J.R. Leventhal, et al.; "Complement Depletion Prolongs Discordant Cardiac Xenograft Survival in Rodents and Non–Human Primates"; *Transplantation Proceedings*; 1993; vol. 25, No. 1, pp. 398–399.
Scott K. Pruitt et al.; "The Effect of Soluble Complement Receptor Type 1 on Hyperacute Rejection of Porcine Xenografts"; *Transplantation*; Feb. 3, 1994; vol. 57, pp. 363–370.

(Continued)

*Primary Examiner*—Joseph Woitach
(74) *Attorney, Agent, or Firm*—Merchant & Gould P.C.

(57) ABSTRACT

The invention relates to nucleic acids which encode glycosyltransferase and are useful in producing cells and organs from one species which may be used for transplantation into a recipient of another species. It also relates to the production of nucleic acids which, when present in cells of a transplanted organ, result in reduced levels of antibody recognition of the transplanted organ.

20 Claims, 12 Drawing Sheets

OTHER PUBLICATIONS

Joseph R. Leventhal et al.; "Removal of Baboon and Human Antiporcine IgG and IgM Natural Antibodies by Immunoadsorption"; *Transplantation*; Jan. 27, 1995, vol. 59, pp. 294–300.

R.J. Brewer et al.; "Depletion of Preformed Antibody in Primates for Discordant Xenotransplantation by Continuous Donor Organ Plasma Perfusion"; *Transplantation Proceedings*; 1993; vol. 25, No. 1, pp. 385–386.

Kenneth R. McCurry et al.; "Human Complement regulatory proteins protect swine–to–primate cardiac xenografts from humoral injury"; *Nature Medicine*; May 5, 1995; vol. 1, No. 5, pp. 423–427.

William L. Fodor et al.; "Expression of a functional human complement inhibitor in a transgenic pig as a model for the prevention of xenogeneic hyperacute organ rejection"; *Proc. Natl. Acad. Sci.*; Nov. 1994; vol. 91, pp. 11153–11157.

Ariella M. Rosengard et al.; "Tissue Expression of Human Complement Inhibitor, Decay–Accelerating Factor, in Transgenic Pigs"; *Transplantation*; May 15, 1995; vol. 59, No. 9, pp. 1325–1333.

Mauro S. Sandrin & Ian F.C. McKenzie; "Gal$\alpha$(1,3)Gal, the Major Xenoantigen(s) Recognised in Pigs by Human Natural Antibodies"; *Immunological Reviews*; 1994; No. 141, pp. 169–190.

Mauro S. Sandrin et al.; "Characterization of cDNA clones for porcine $\alpha$(1,3)galactosyl transferase: The enzyme generating the Gal$\alpha$(1,3)Gal epitope"; *Xenotransplantation*; 1994; pp. 81–88.

David H. Joziasse et al.; "Characterization of an $\alpha 1 \rightarrow 3$–Galactosyltransferase Homologue on Human Chromosome 12 That Is Organized as a Processed Pseudogene"; *Journal of Biological Chemistry*; 1991; vol. 266, No. 11, pp. 6991–6998.

Robert D. Larsen et al.; "Framshift and Nonsense Mutations in a Human Genomic Sequence Homologous to a Murine UDP–Gal:$\beta$–D–Gal(1,4)–D–GlcNAc $\alpha$(1,3)–Galactosyltransferase cDNA"; *Journal of Biological Chemistry*; 1990; vol. 265, No. 12, pp. 7055–7061.

Mauro S. Sandrin et al.; "Enzymatic remodelling of the carbohydrate surface of a xenogenic cell substantially reduces human antibody binding and complement–mediated cytolysis"; *Nature Medicine*; Dec. 1995; vol. 1, No. 12, pp. 1261–1267.

Mauro S. Sandrin, William L. Fodor, Effie Mouhtouris, Narin Osman, Shlomo Cohney, Scott A. Rollins, Edward R. Guilmette, Eva Setter, Stephen P. Squinto & Ian F.C. McKenzie; Enzymatic remodelling of the carbohydrate surface of a xenogenic cell substantially reduces human antibody binding and complement–mediated cytolysis; *Nature Medicine*; Dec. 1995; vol. 1, No. 12, pp. 1261–1267.

Jo Burke, John M. Pettitt, Danielle Humphris, and Paul A. Gleeson; "Medial–Golgi Retention on N–Acetylglucosaminyltransferase I"; *Journal of Biological Chemistry*; Apr. 22, 1994; vol. 269, No. 16, pp. 12049–12059.

Narin Osman, Ian F.C. McKenzie, Effie Mouhtouris, and Mauro S. Sandrin; "Switching Amino–terminal Cytoplasmic Domains of $\alpha$(1,2) Fucosyltransferase and $\alpha$(1,3) Galactosyltransferase Alters the Expression of H Substance and Gal$\alpha$(1,3)Gal"; *Journal of Biological Chemistry*; Dec. 20, 1996; vol. 271, No. 51, pp. 33105–33109.

Mauro S. Sandrin et al.; "Anti–pig IgM antibodies in human serum react predominantly with Gal($\alpha$1–3)Gal epitopes"; *Proc. Natl. Acad. Sci.*; Dec. 1993; vol. 90, pp. 11391–11395.

Mauro S. Sandrin et al.; "Identification of Gal($\alpha$1,3)Gal as the Major Epitope for Pig–to–Human Vascularised Xenografts"; *Transplantation Reviews*; 1994; vol. 8, No. 3, pp. 134–149.

DKC Cooper et al.; "Identification of$\alpha$–galactosyl and other carbohydrate epitopes that are bound by human anti–pig antibodies: relevance to discordant xenografting in man"; *Transplant Immunology*; 1993; pp. 198–205.

David K.C. Cooper et al.; "Oligosaccharides and Discordant Xenotransplantation"; *Immunological Reviews*; 1994; No. 141, pp. 31–58.

Uri Galili et al.; "Evolutionary relationship between the natural anti–Gal antibody and the Gal$\alpha 1 \rightarrow 3$Gal epitope in primates"; *Proc. Natl. Acad. Sci.*; Mar. 1987; vol. 84, pp. 1369–1373.

Uri Galili et al.; "Man, apes, and Old World Monkeys Differ from Other Mammals in the Expression of $\alpha$–Galactosyl Epitopes on Nucleated Cells"; *Journal of Biological Chemistry*; 1988; vol. 263, No. 33, pp. 17755–17762.

Robert d. Larsen et al.; "Isolation of a cDNA encoding a muring UDPgalactose:$\beta$–D–galactosyl–1,4–N–acetyl–D–glucosaminide $\alpha$–1,3–galactosyltransferase: Expression cloning by gene transfer"; *Proc. Natl. Acad. Sci.*; Nov. 1989; vol. 86, pp. 8227–8231.

David H. Joziasse et al.; "Murine $\alpha$1,3–Galactosyltransferase"; *Journal of biological Chemistry*, 1992; vol. 267, No. 8, pp. 5534–5541.

David H. Joziasse et al.; "Bovine $\alpha 1 \rightarrow 3$–Galactosyltransferase: Isolation and Characterization of a cDNA Clone"; *Journal o Biological Chemistry*; 1989; vol. 264, No. 24, pp. 14290–14297.

C. Kioke et al.; "Introduction of $\alpha$(1,2)–fucosyltransferase and its effect on $\alpha$–Gal epitopes in transgenic pig"; *Xenotransplantation*; 1996; pp. 81–86.

Shlomo Cohney et al.; "Molecular cloning of the gene coding for pig $\alpha 1 \rightarrow 2$fucosyltransferase"; *Immunogenetics*; 1996; pp. 76–79.

Robert D. Larsen et al.; "Molecular cloning, sequence, and expression of a human GDP–L–fucose:$\beta$–D–galactoside 2–$\alpha$–L–fucosyltransferase cDNA that can form the H blood group antigen"; *Proc. Natl. Acad. Sci.*; Sep. 1990; vol. 87, pp. 6674–6678.

Colleen E. Hayes et al.; "An $\alpha$–D–Galactosyl–binding Lectin from *Bandeiraea simplicifolia* Seeds"; *Journal of Biological Chemistry*, 1974; vol. 249, No. 6, pp. 1904–1914.

Marion M. Bradford; "A Rapid and Sensitive Method for the Quantitation of Microgram Quantities of Protein Utilizing the Principle of Protein–Dye Binding"; *Analytical Biochemistry*, 1976; pp. 248–254.

Valanila P. Rajan et al.; "A Cloned Human DNA Restriction Fragment Determines Expression of a GDP–L–fucose:$\beta$–D–Galactoside 2–$\alpha$–L–fucosyltransferase in Transfected Cells"; *Journal of Biological Chemistry*; 1989; vol. 264, No. 19, pp. 11158–11167.

Dirk H. Van Den Eijnden et al.; "Identification and Characterization of an UDP–gal:N–Acetyllactosaminide $\alpha$–1, 3–D–Galactosyltransferase in Calf Thymus"; *Eur. J.. Biochem.*; 1983; pp. 523–530.

Timothy R. Henion et al.; "Defining the minimal size of catalytically active primate $\alpha$1,3 galactosyltransferase: structure–function studies on the recombinant truncated enzyme"; *Glycobiology*; 1994; vol. 4, No. 2, pp. 193–201.

Harry Schachter; "Molecular cloning of glycosyltransferase genes"; Oxford University Press; 1994; pp. 88–162.

Jo Burke et al.; "The Transmembrane and Flanking Sequences of β1,2-N-Acetylglucosaminyltransferase 1 Specify medial-Golgi Localization"; *Journal of Biological Chemistry*; 1992; vol. 267, No. 34, pp. 24433–24440.

Bor Luen Tang et al; "The Transmembrane Domain of N-Glucosaminyltransferase 1 Contains a Golgi Retention Signal"; *Journal of biological Chemistry*; 1992; vol. 267, No. 14, pp. 10122–10126.

Tommy Nilsson et al.; "The membrane spanning domain of β-1,4-galactosyltransferase specifies trans Golgi localization"; *EMBO Journal*; 191; vol. 10, No. 12, pp. 3567–3575.

Daisuke Aoki et al.; "Golgi retention of a trans-Golgi membrane protein, galactosyltransferase, requires cysteine and histidine residues within the membrane-anchoring domain"; *Proc. Natl. Acad. Sci.*; May 1992; vol. 89, pp. 4319–4323.

Rohan D. Teasdale et al.; "The Signal for Golgi Retention of Bovine β1,4-Galactosyltransferase Is in the Transmembrane Domain"; *Journal of biological Chemistry*; 1992; vol. 267, No. 6, pp. 4084–4096.

Hugh r. B. Pelham; "The retention signal for soluble proteins of the endoplasmic reticulum"; *Trends Biochem. Sci.*; 1990; pp. 483–486.

Michael R. Jackson et al; "Identification of a consensus motif for retntion of transmembrane proteins in the endoplasmic reticulum"; *EMBO Journal*; 1990; vol. 9, No. 10, pp. 3153–3162.

Felix Kappeler et al.; "A dual Role for COOH-terminal Lysine Residues in pre-Golgi Retention and endocytosis of ERGIC-53"; *Journal of biological Chemistry*; 1994; vol. 269, No. 9, pp. 6279–6281.

Kari F. Johnson et al.; "A His-Leu-Leu Sequence near the carboxyl Terminus of the Cytoplasmic Domain of the Cation-dependent Mannose 6-Phosphate Receptor Is Necessary for the Lysosomal Enzyme Sorting Function"; *Journal of biological Chemistry*; 1992; vol. 267, No. 24, pp. 17110–17115.

Sean Munro; "Sequences within and adjacent to the transmembrane segment of α-2,6-sialyltransferase specify Golgi retention"; *EMBO Journal*; 1991; vol. 10, No. 12, pp. 3577–3588.

Refka Y. Dahdal et al.; "Specific Sequences in the Signal Anchor of the β-Galactoside α-2,-Sialyltransferase Are Not Essential for Golgi Localization"; *Journal of Biological Chemistry*; 1993; vol. 268, No. 35, pp. 26310–26319.

Isamu Matsumoto et al.; "Purification and Characterization of an Anti-H(o) Phytohemagglutinin of Ulex Europeus"; *Biochimica et Biophysica Acta*; 1969; pp. 180–189.

Tommy Nilsson et al.; "Overlapping Distribution of Two Glycosyltransferases in the Golgi Apparatus of HeLa Cells"; *Journal of Cell Biology*; 1993; vol. 120, No. 1, pp. 5–13.

A.H. Good, et al.; "Identification of Carbohydrate Structures That Bind Human Antiporcine Antibodies: Implications for Discordant Xenografting in Humans"; *Transplantation Proceedings*; Apr. 1991; vol. 24, No. 2, pp. 559–562.

* cited by examiner

PORCINE SECRETOR SEQUENCE (SEQ. I.D. NOS: 1 and 2)

```
          M   L   S   M   Q   A   S   F   F   F   P   T   G   P   F   I   L    17
CT ACA GCC ATG CTC AGC ATG CAG GCA TCC TTC TTC TTC CCC ACG GGT CCC TTC ATC CTC   59

F   V   F   T   A   S   T   I   F   H   L   Q   Q   R   N   V   K   I   Q   P    37
TTT GTC TTC ACG GCT TCC ACC ATA TTT CAC CTT CAG CAG AGG ATG GTG AAG ATT CAA CCC  119

T   W   E   L   Q   M   V   T   Q   V   T   T   E   S   P   S   S   P   Q   L    57
ACG TGG GAG TTA CAG ATG GTG ACG CAG GTG ACA GAG ACC GAG AGC CCC TCG AGC CCC CAG CTG  179
```

PORCINE SECRETOR SEQUENCE

```
  K   G   N   W   T   I   N   A   I   G   R   L   G   N   Q   M   G   E   Y   A    77
AAG GGC ATG TGG ACG ATC AAT GCC ATC GGC CGC CTG GGG AAC CAG ATG GGG GAG TAC GCC  239

T   L   Y   A   L   A   R   M   N   G   R   P   A   F   I   P   P   E   M   H    97
ACC CTG TAC GCG CTG GCC AGG ATG AAC GGG CGG CCG GCC TTC ATC CCG CCC GAG ATG CAC  299

S   T   L   A   P   I   F   F   R   I   T   L   P   V   L   H   A   S   T   A   R   117
AGC ACG CTG GCC CCC ATC TTC TTC AGG ATC ACC CTC CCG GTC CTG CAC GCC AGC ACG GCC CGC   359

R   I   P   W   Q   N   Y   H   L   N   D   W   N   E   E   R   Y   R   H   I    137
AGG ATC CCC TGG CAG AAC TAC CAC CTG AAC GAC TGG AAT GAG GAG CGG TAC CGC CAC ATC   419

```
CCG GGG GAG TAC GTG CGC CTC ACG GGC TAC CCC TGC TCC TGG ACC TTC TAC GAC CAC CTG  479
 R   T   E   I   L   R   E   F   T   L   H   N   H   V   R   E   E   A   Q   D   177

CGC ACC GAG ATC CTC CGG GAG TTC ACC CTG CAT AAC CAC GTG CGC GAG GAG GCC CAG GAT  539
 R   T   E   I   L   R   E   F   T   L   H   N   H   V   R   E   E   A   Q   D   197

TTC CTG CGG GGT CTG CGG GTG AAC GGG AGC CGA CCG AGT ACC TAC GTG GGG GTG CAC GTG  599
 F   L   R   G   L   R   V   N   G   S   R   P   S   T   Y   V   G   V   H   V   197

CGC CGG GGG GAC TAC GTG CAC GTG CAC CTG ATG CCC AAC GTG TGG AAG GGC GTG GCC GAC CGG  659
 R   R   G   D   Y   V   H   V   M   P   N   V   W   K   G   V   A   D   R   217

CGG TAC CTG GAG CAG GCC CTG GAC TGG TTC CGG GCT CGC TAC CGC TCC CCC GTC TTT GTG  719
 R   Y   L   E   Q   A   L   D   W   F   R   A   R   Y   R   S   P   V   F   V   237

GTC TCC AGC AAC GGC ATG GCC ATG GAG GCC TGG TGT CGG GAA AAC ATC AAT GCC TCG CGC GGC GAT GTG  779
 V   S   S   N   G   M   A   W   C   R   E   N   I   N   A   S   R   G   D   V   257

GTG TTT GCC GGC AAT GGC ATC GAG ACG TTC GGG ATC TGG GCC GCC TAC CTT GCT GGT  839
 V   F   A   G   N   G   I   E   G   T   F   G   I   W   A   A   Y   L   A   G   277

TGT AAC CAC ACT GTC ATG ACC ATT GGC ACG TTC GGG ATC TGG GCC GCC TAC CTT GCT GGT  899
 C   N   H   T   V   M   T   I   G   T   F   G   I   W   A   A   Y   L   A   G   297

GGA GAG ACC ATC TAC CTG GCC AAT TAC ACG CTC CCG GAC TCT CCC TTC CTC AAA CTC TTT  959
 G   E   T   I   Y   L   A   N   Y   T   L   P   D   S   P   F   L   K   L   F   317
```

FIGURE 6 (cont.)

```
    K   P   E   A   A   F   L   P   E   W   I   G   I   E   A   D   L   S   P   L   337
    AAG CCC GAG GCA GCC TTC CTG CCC GAG TGG ATT GGG ATC GAG GCA GAC CTG TCC CCA CTC 1019

L   K   H   *                                                                  340
    CTT AAG CAC TGA TGT CGG CTG TCC                                                 1043
```

FIGURE 6 (cont.)

FIG.7
PIG H TRANSFERASE (SEQ. I.D. NOS: 3 and 4)

```
  M   W   V   P   S   R   R   H   L   C   L   T   F   L   L   V   C   V   L   A         20
ATGTGGGTCCCCAGCCGCCGCCACCTCTGTCTGACCTTCCTGCTAGTCTGTGTTTTAGCA                            60

A   I   F   F   L   N   V   Y   Q   D   L   F   Y   S   G   L   D   L   L   A         40
GCAATTTTCTTCCTGAACGTCTATCAAGACCTCTTTTACAGTGGCTTAGACCTGCTGGCC                           120

L   C   P   D   H   N   V   V   S   S   P   V   A   I   F   C   L   A   G   T         60
CTGTGTCCAGACCATAACGTGGTATCATCTCCCGTGGCCATATTCTGCCTGGCGGGCACG                           180

P   V   H   P   N   A   S   D   S   C   P   K   H   P   A   S   F   S   G   T         80
CCGGTACACCCCAACGCCTCCGATTCCTGTCCCAAGCATCCTGCCTCCTTTTCCGGGACC                           240

W   T   I   Y   P   D   G   R   F   G   N   Q   M   G   Q   Y   A   T   L   L        100
TGGACTATTTACCCGGATGGCCGGTTTGGGAACCAGATGGGACAGTATGCCACGCTGCTG                           300

A   L   A   Q   L   N   G   R   Q   A   F   I   Q   P   A   M   H   A   V   L        120
GCCCTGGCGCAGCTCAACGGCCGCCAGGCCTTCATCCAGCCTGCCATGCACGCCGTCCTG                           360

A   P   V   F   R   I   T   L   P   V   L   A   P   E   V   D   R   E   A   I        140
GCCCCCGTGTTCCGCATCACGCTGCCTGTCCTGGCGCCCGAGGTAGACAGGCACGCTCCT                           420

W   R   E   L   E   L   H   D   W   M   S   E   D   Y   A   H   L   K   R   P        160
TGGCGGGAGCTGGAGCTTCACGACTGGATGTCCGAGGATTATGCCCACTTAAAGGAGCCC                           480

W   L   K   L   T   G   F   P   C   S   W   T   F   F   H   H   L   R   E   Q        180
TGGCTGAAGCTCACCGGCTTCCCCTGCTCCTGGACCTTCTTCCACCACCTCCGGGAGCAG                           540

I   R   S   E   F   T   L   H   D   H   L   R   Q   E   A   Q   G   V   L   S        200
ATCCGCAGCGAGTTCACCCTGCACGACCACCTTCGGCAAGAGGCCCAGGGGGTACTGAGT                           600

Q   F   R   L   P   R   T   G   D   R   P   S   T   F   V   G   V   H   V   R        220
CAGTTCCGTCTACCCCGCACAGGGGACCGCCCCAGCACCTTCGTGGGGGTCCACGTGCGC                           660

R   G   D   Y   L   R   V   M   P   K   R   W   K   G   V   V   G   D   G   A        240
CGCGGGGACTATCTGCGTGTGATGCCCAAGCGCTGGAAGGGGGTGGTGGGTGACGGCGCT                           720

Y   L   Q   Q   A   M   D   W   F   R   A   R   Y   E   A   P   V   F   V   V        260
TACCTCCAGCAGGCTATGGACTGGTTCCGGGCCCGATACGAAGCCCCCGTCTTTGTGGTC                           780

T   S   N   G   M   E   W   C   R   K   N   I   D   T   S   R   G   D   V   I        280
ACCAGCAACGGCATGGAGTGGTGCCGGAAGAACATCGACACCTCCCGGGGGGACGTGATC                           840

F   A   G   D   G   R   E   A   A   P   A   R   D   F   A   L   L   V   Q   C        300
TTTGCTGGCGATGGGCGGGAGGCCGCGCCCGCCAGGGACTTTGCGCTGCTGGTGCAGTGC                           900

N   H   T   I   M   T   I   G   T   F   G   F   W   A   A   Y   L   A   G   G        320
AACCACACCATCATGACCATTGGCACCTTCGGCTTCTGGGCCGCCTACCTGGCTGGTGgA                           960

D   T   I   Y   L   A   N   F   T   L   P   T   S   S   F   L   K   I   P   K        340
GATACcATCTACTTGGCTAACTTCACCCTGCCcACTTCCAGCTTCCTGAAGATCTTTAAA                          1020

P   E   A   A   F   L   F   E   W   V   G   I   N   A   D   L   S   P   L   Q        360
CcCGAGGCTGCCTTCCTGCCCGAGTGGGTGGGCATTAATGCAGACTTGTCTCCACTCCAG                          1080

M   L   A   G   P   I                                                                365
ATGTTGGCTGGGCCTTGA                                                                    1098
```

… # NUCLEIC ACIDS ENCODING A CHIMERIC GLYCOSYLTRANSFERASE

CROSS REFERENCE TO RELATED APPLICATIONS

This application is a § 371 national stage filing based on PCT/AU97/00492, filed Aug. 1, 1997, which claims priority through provisional application No. 60/024,279, filed Aug. 21, 1996 and Australian application PO 1402, filed Aug. 2, 1996.

FIELD OF THE INVENTION

The present invention relates to nucleic acids which encode glycosyltransferase and are useful in producing cells and organs from one species which may be used for transplantation into a recipient of another species. Specifically the invention concerns production of nucleic acids which, when present in cells of a transplanted organ, result in reduced levels of antibody recognition of the transplanted organ.

BACKGROUND OF THE INVENTION

The transplantation of organs is now practicable, due to major advances in surgical and other techniques. However, availability of suitable human organs for transplantation is a significant problem. Demand outstrips supply. This has caused researchers to investigate the possibility of using non-human organs for transplantation.

Xenotransplantation is the transplantation of organs from one species to a recipient of a different species. Rejection of the transplant in such cases is a particular problem, especially where the donor species is more distantly related, such as donor organs from pigs and sheep to human recipients. Vascular organs present a special difficulty because of hyper-acute rejection (HAR).

HAR occurs when the complement cascade in the recipient is initiated by binding of antibodies to donor endothelial cells.

Previous attempts to prevent HAR have focused on two strategies: modifying the immune system of the host by inhibition of systemic complement formation (1,2), and antibody depletion (3,4). Both strategies have been shown to prolong xenograft survival temporarily. However, these methodologies are therapeutically unattractive in that they are clinically impractical, and would require chronic immunosuppressive treatments. Therefore, recent efforts to inhibit HAR have focused on genetically modifying the donor xenograft. One such strategy has been to achieve high-level expression of species-restricted human complement inhibitory proteins in vascularized pig organs via transgenic engineering (5–7). This strategy has proven to be useful in that it has resulted in the prolonged survival of porcine tissues following antibody and serum challenge (5,6). Although increased survival of the transgenic tissues was observed, long-term graft survival was not achieved (6). As observed in these experiments and also with systemic complement depletion, organ failure appears to be related to an acute antibody-dependent vasculitis (1,5).

In addition to strategies aimed at blocking complement activation on the vascular endothelial cell surface of the xenograft, recent attention has focused on identification of the predominant xenogeneic epitope recognised by high-titre human natural antibodies. It is now accepted that the terminal galactosyl residue, Gal-$\alpha$(1,3)-Gal, is the dominant xenogeneic epitope (8–15). This epitope is absent in Old World primates and humans because the $\alpha$(1,3)-galactosyltransferase (gal-transferase or GT) is non-functional in these species. DNA sequence comparison of the human gene to $\alpha$(1,3)-galactosyltransferase genes from the mouse (16,17), ox (18), and pig (12) revealed that the human gene contained two frameshift mutations, resulting in a nonfunctional pseudogene (20,21). Consequently, humans and Old World primates have pre-existing high-titre antibodies directed at this Gal-$\alpha$(1,3)-Gal moiety as the dominant xenogeneic epitope.

One strategy developed was effective to stably reduce the expression of the predominant Gal-$\alpha$(1,3)-Gal epitope. This strategy took advantage of an intracellular competition between the gal-transferase and $\alpha$(1,2)-fucosyltransferase (H-transferase) for a common acceptor substrate. The gal-transferase catalyzes the transfer of a terminal galactose moiety to an N-acetyl lactosamine acceptor substrate, resulting in the formation of the terminal Gal-$\alpha$(1,3)-Gal epitope. Conversely, H-transferase catalyzes the transfer of a fucosyl residue to the N-acetyl lactosamine acceptor substrate, and generates a fucosylated N-acetyl lactosamine (H-antigen, i.e., the O blood group antigen), a glycosidic structure that is universally tolerated. Although it was reported that expression of human H-transferase transfected cells resulted in high level expression of the non-antigenic H-epitope and significantly reduced the expression of the Gal-$\alpha$(1,3)-Gal xenoepitope, there are still significant levels of Gal-$\alpha$(1,3)-Gal epitope present on such cells.

SUMMARY OF THE INVENTION

In view of the foregoing, it is an object of the present invention to further reduce levels of undesirable epitopes in cells, tissues and organs which may be used in transplantation.

In work leading up to the invention the inventors surprisingly discovered that the activity of H transferase may be further increased by making a nucleic acid which encodes a H transferase catalytic domain but is anchored in the cell at a location where it is better able to compete for substrate with gal transferase. Although work by the inventors focused on a chimeric H transferase, other glycosyltransferase enzymes may also be produced in accordance with the invention.

Accordingly, in a first aspect the invention provides a nucleic acid encoding a chimeric enzyme, wherein said chimeric enzyme comprises a catalytic domain of a first glycosyltransferase and a localization signal of a second glycosyltransferase, whereby when said nucleic acid is expressed in a cell said chimeric enzyme is located in an area of the cell where it is able to compete for substrate with a second glycosyltransferase, resulting in reduced levels of a product from said second glycosyltransferase.

Preferably the nucleic acid is in an isolated form; that is the nucleic acid is at least partly purified from other nucleic acids or proteins.

Preferably the nucleic acid comprises the correct sequences for expression, more preferably for expression in a eukaryotic cell. The nucleic acid may be present on any suitable eukaryotic expression vector such as pcDNA (Invitrogen). The nucleic acid may also be present or other vehicles whether suitable for eukaryotes or not, such as plasmids, phages and the like.

Preferably the catalytic domain of the first glycosyltransferase is derived from H transferase, secretor sialyltransferase, a galactosyl sulphating enzyme or a phosphorylating enzyme.

The nucleic acid sequence encoding the catalytic domain may be derived from, or similar to a glycosyltransferase from an species. Preferably said species is a species such as human or other primate species, including Old World monkeys, or other mammals such as ungulates (for example pigs, sheep, goats, cows, horses, deer, camels) or dogs, mice, rats and rabbits. The term "similar to" means that the nucleic acid is at least partly homologous to the glycosyltransferase genes described above. The term also extends to fragments of and mutants, variants and derivatives of the catalytic domain whether naturally occurring or man made.

Preferably the localization signal is derived from a glycosyltransferase which produces glycosylation patterns which are recognised as foreign by a transplant recipient. More preferably the localization signal is derived from α(1,3) galactosyltransferase. The effect of this is to down-regulate the level of Gal-α(1,3)-Gal produced in a cell when the nucleic acid is expressed by the cell.

The nucleic acid sequence encoding the localization signal may be derived from any species such as those described above. Preferably it is derived from the same species as the cell which the nucleic acid is intended to transform i.e., if pig cells are to be transformed, preferably the localization signal is derived from pig.

More preferably the nucleic acid comprises a nucleic acid sequence encoding the catalytic domain of H transferase and a nucleic acid sequence encoding a localization signal from Gal transferase. Still more preferably both nucleic acid sequences are derived from pigs. Even more preferably the nucleic acid encodes gtHT described herein.

The term "nucleic acid" refers to any nucleic acid comprising natural or synthetic purines and pyrimidines. The nucleic acid may be DNA or RNA, single or double stranded or covalently closed circular.

The term "catalytic domain" of the chimeric enzyme refers to the amino acid sequences necessary for the enzyme to function catalytically. This comprises one or more contiguous or non-contiguous amino acid sequences. Other non-catalytically active portions also may be included in the chimeric enzyme.

The term "glycosyltransferase" refers to a polypeptide with an ability to move carbohydrates from one molecule to another.

The term "derived from" means that the catalytic domain is based on, or is similar, to that of a native enzyme. The nucleic acid sequence encoding the catalytic domain is not necessarily directly derived from the native gene. The nucleic acid sequence may be made by polymerase chain reaction (PCR), constructed de novo or cloned.

The term "localization signal" refers to the amino acid sequence of a glycosyltransferase which is responsible for anchoring it in location within the cell. Generally localization signals comprise amino terminal "tails" of the enzyme. The localization signals are derived from a second glycosyltransferase, the activity of which it is desired to minimise. The localization of a catalytic domain of a first enzyme in the same area as the second glycosyltransferase means that the substrate reaching that area is likely to be acted or by the catalytic domain of the first enzyme, enabling the amount of substrate catalysed by the second enzyme to be reduced.

The term "area of the cell" refers to a region, compartment or organelle of the cell. Preferably the area of the cell is a secretory organelle such as the Golgi apparatus.

In another aspect the invention provides an isolated nucleic acid molecule encoding a localization signal of a glycosyltransferase. Preferably the signal encoded comprises an amino terminus of said molecule; more preferably it is the amino terminus of gal transferase. The gal transferase may be described from or based on a gal transferase from any mammalian species, such as those described above. Particularly preferred sequences are those derived from pig, mouse or cattle.

In another aspect the invention relates to a method of producing a nucleic acid encoding a chimeric enzyme said enzyme comprising a catalytic domain of a first glycosyltransferase and a localization signal of a second glycosyltransferase whereby when said nucleic acid is expressed in a cell said chimeric enzyme is located in an area of the cell where it is able to compete for substrate with a second glycosyltransferase said method comprising operably linking a nucleic acid sequence encoding a catalytic domain from a first glycosyltransferase to a nucleic acid sequence encoding a localization signal of a second glycosyltransferase.

The term "operably linking" means that the nucleic acid sequences are ligated such that a functional protein is able to be transcribed and translated.

Those skilled in the art will be aware of various techniques for producing the nucleic acid. Standard techniques such as those described in Sambrook et al may be employed.

Preferably the nucleic acid sequences are the preferred sequences described above.

In another aspect the invention provides a method of reducing the level of a carbohydrate exhibited on the surface of a cell, said method comprising causing a nucleic acid to be expressed in said cell wherein said nucleic acid encodes a chimeric enzyme which comprises a catalytic domain of a first glycosyltransferase and a localization signal of a second glycosyltransferase, whereby said chimeric enzyme is located in an area of the cell where it is able to compete for substrate with said second glycosyltransferase, and wherein said second glycosyltransferase is capable of producing said carbohydrate.

The term "reducing the level of a carbohydrate" refers to lowering, minimising, or in some cases, ablating the amount of carbohydrate displayed on the surface of the cell. Preferably said carbohydrate is capable of stimulating recognition of the cell as "non-self" by the immune system of an animal. The reduction of such a carbohydrate therefore renders the cell, or an organ composed of said cells, more acceptable to the immune system of a recipient animal in a transplant situation or gene therapy situation.

The term "causing a nucleic acid to be expressed" means that the nucleic acid is introduced into the cell (i.e. by transformation/transfection or other suitable means) and contains appropriate signals to allow expression in the cells.

The cell may be any suitable cell, preferably mammalian, such as that of a New World monkey, ungulate (pig, sheep, goat, cow, horse, deer, camel, etc.) or other species such as dogs.

In another aspect the invention provides a method of producing a cell from one species (the donor) which is immunologically acceptable to another species (the recipient) by reducing levels of carbohydrate on said cell which cause it to be recognised as non-self by the other species, said method comprising causing a nucleic acid to be expressed in said cell wherein and nucleic acid encodes a chimeric which comprises a catalytic domain of a first glycosyltransferase and a localization signal of a second glycosyltransferase, whereby said chimeric enzyme is located in an area of the cell where it is able to compete for substrate with said second glycosyltransferase, and wherein said second glycosyltransferase is capable of producing said carbohydrate.

The term "immunologically acceptable" refers to producing a cell, or an organ made up of numbers of the cell, which does not cause the same degree of immunological reaction in the recipient species as a native cell from the donor species. Thus the cell may cause a lessened immunological reaction, only requiring low levels of immunosuppressive therapy to maintain such a transplanted organ or no immunosuppression therapy.

The cell may be from any of the species mentioned above. Preferably the cell is from a New World primate or a pig. More preferably the cell is from a pig.

The invention extends to cells produced by the above method and also to organs comprising the cells.

The invention further extends to non-human transgenic animals harbouring the nucleic acid of the invention. Preferably the species is a human, ape or Old World monkey.

The invention also extends to the proteins produced by the nucleic acid. Preferably the proteins are in an isolated form.

In another aspect the invention provides an expression unit which expresses the nucleic acid of the invention, resulting in a cell which is immunologically acceptable to an animal having reduced levels of a carbohydrate on its surface, which carbohydrate is recognized as non-self by said species. In a preferred embodiment, the expression unit is a retroviral packaging cell, cassette, a retroviral construct or retroviral producer cell.

Preferably the species is a human, ape or Old World monkey.

The retroviral packaging cells or retroviral producer cells may be cells of any animal origin where it is desired to reduce the level of carbohydrates on its surface to make it more immunologically acceptable to a host. Such cells may be derived from mammals such as canine, rodent or ruminant species and the like.

The retroviral packaging and/or producer cells may be used in applications such as gene therapy. General methods involving use of such cells are described in PCT/US95/07554 and the references discussed therein.

The invention also extends to a method of producing a retroviral packaging cell or a retroviral producer cell having reduced levels of a carbohydrate on its surface wherein the carbohydrate is recognised as non-self by a species, comprising transforming/transfecting a retroviral packaging cell or a retroviral producer cell with the nucleic acid of the invention under conditions such that the chimeric enzyme is produced.

The diagram shows normal glycosyltransferases porcine $\alpha(1,3)$galactosyltransferase (GT) and human $\alpha(1,2)$ fucosyltransferase (HT), and chimeric transferases ht-GT in which the cytoplasmic domain of GT has been completely replaced by the cytoplasmic domain of HT, and gt-HT in which the cytoplasmic domain of HT has been entirely replaced by the cytoplasmic domain of GT. The protein domains depicted are cytoplasmic domain CYTO, trans-membrane domain TM, stem region STEM, catalytic domain CATALYTIC. The numbers refer to the amino acid sequence of the corresponding normal transferase.

Figure 2:
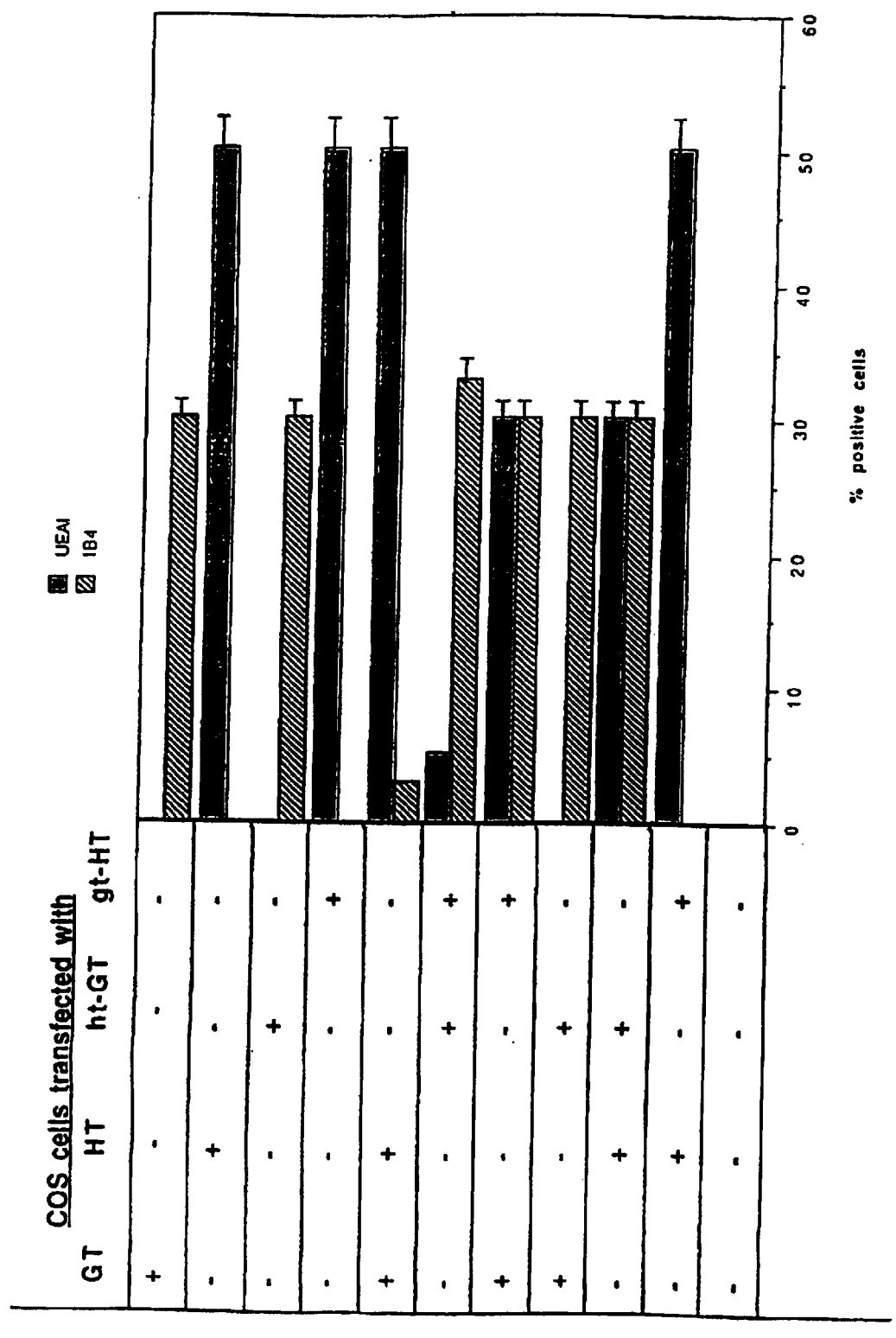

FIG. 2 Cell surface staining of COS cells transfected with normal and chimeric transferases Cells were transfected with normal GT or HT or with chimeric transferases gt-HT or ht-GT and 48 h later were stained with FITC-labelled lectin IB4 or UEAI. Positive-staining cells were visualized and counted by fluorescence microscopy. Results are from at least three replicates and values are+/−SEM.

Figure 3:
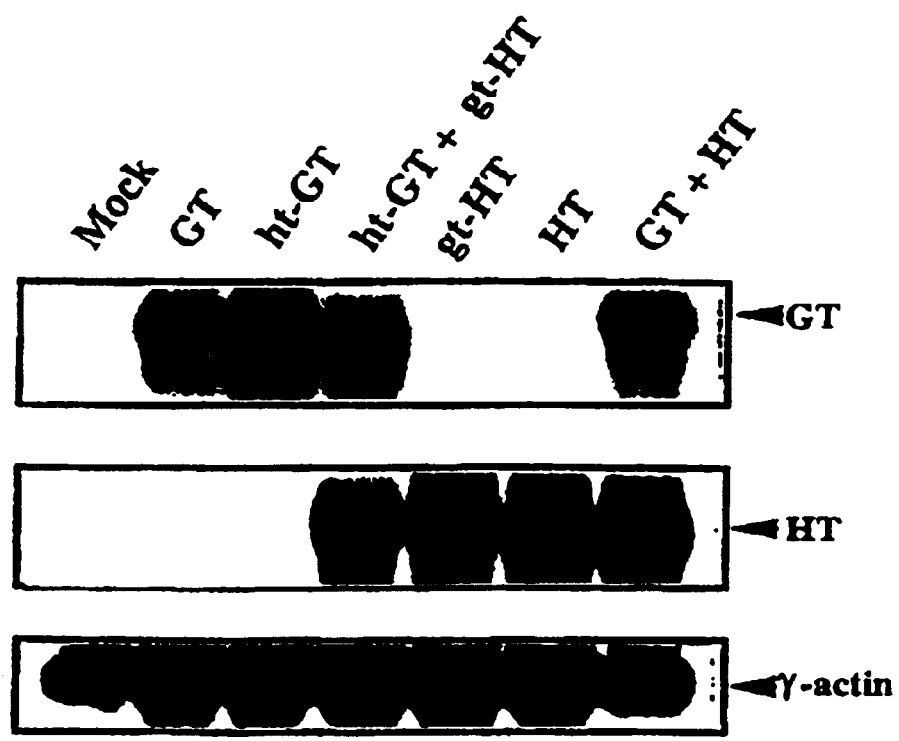

FIG. 3. RNA analysis of transfected COS cells

Northern blots were performed on total RNA prepared from COS cells transfected: Mock, mock-transfected; GT, transfected with wild-type GT; GT1-6/HT, transfected with chimeric transferase gt-HT; GT1-6/HT+HT1-8/GT, co-transfected with both chimeric transferases gt-HT and ht-GT; HT1-8/GT, transfected with chimeric transferase ht-GT; HT, transfected with normal HT; GT+HT co-transfected with both normal transferases GT and HT. Blots were probed with a cDNA encoding GT (Top panel), HT (Middle panel) or g-actin (Bottom panel).

Figure 4:
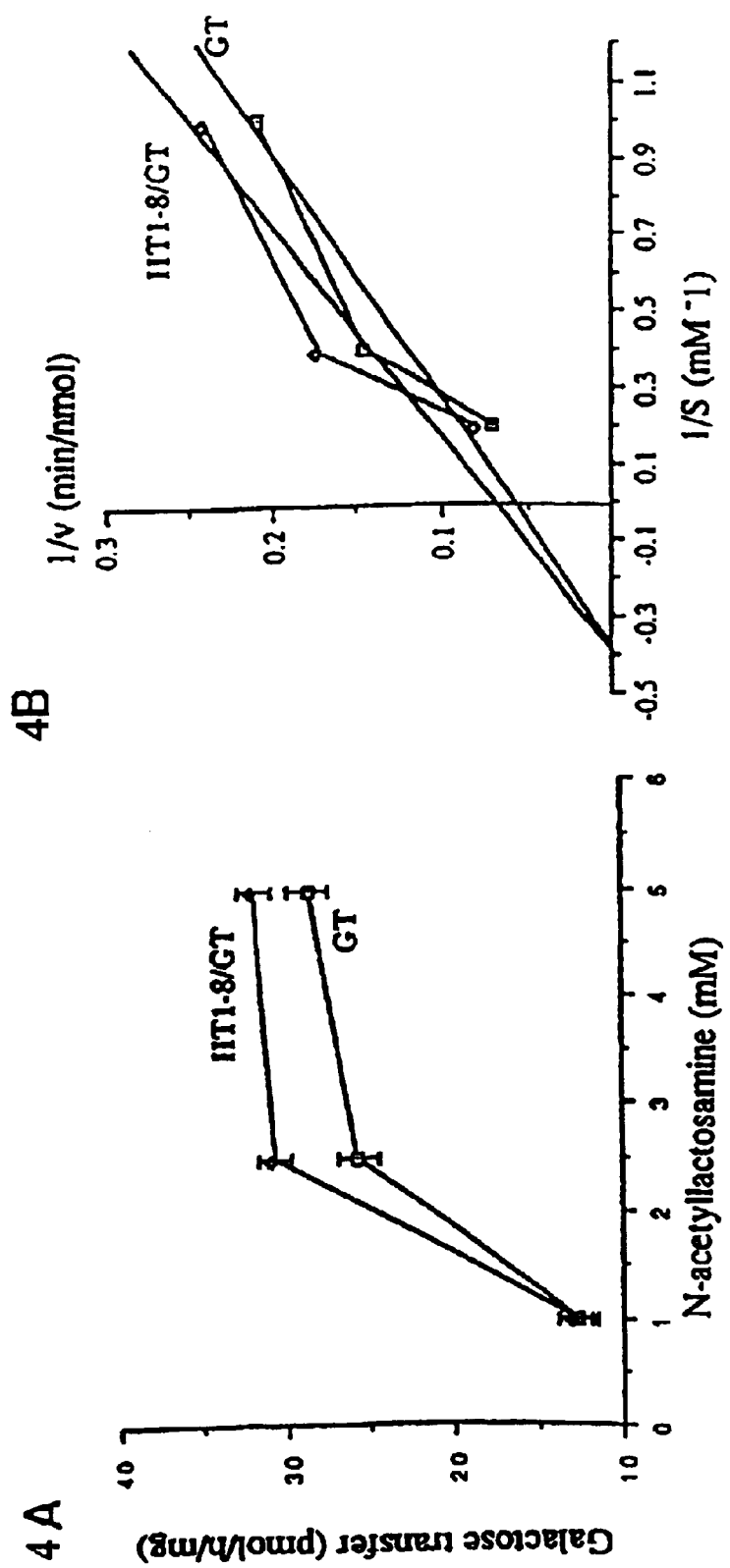
Figure 4:
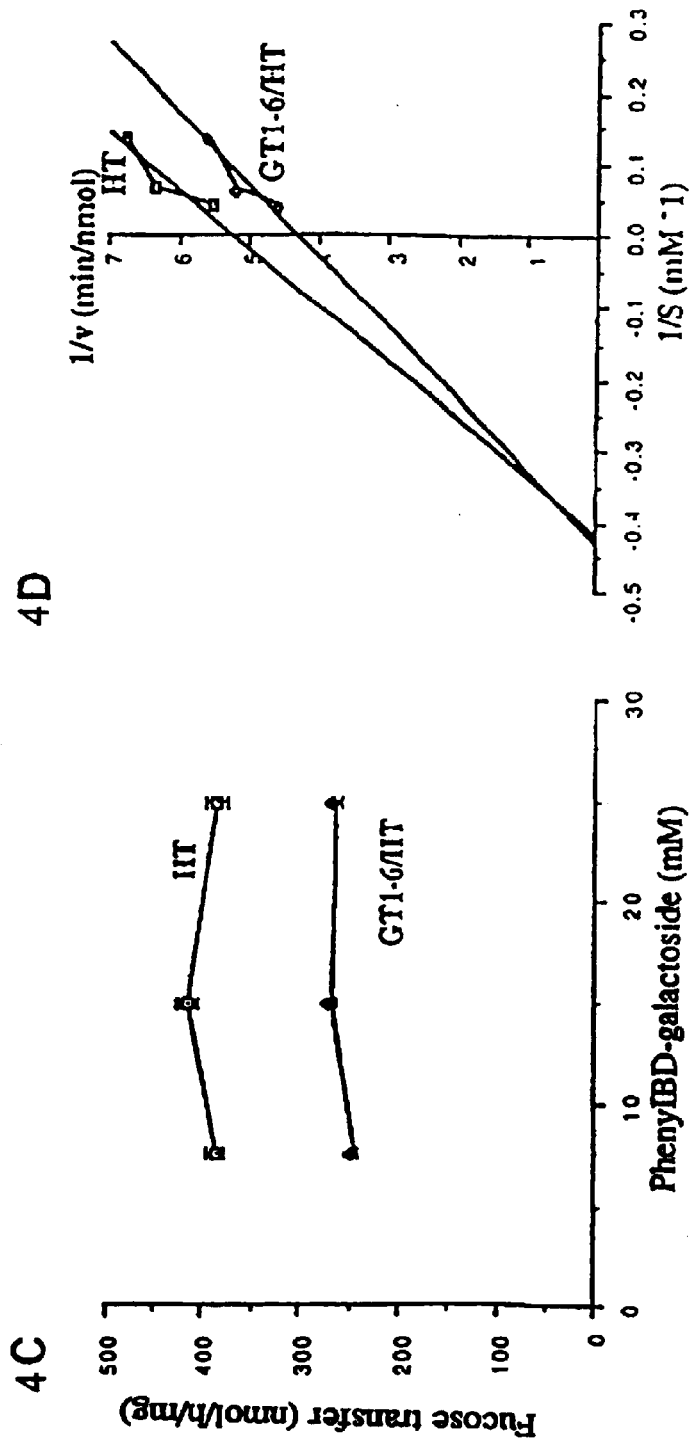

FIG. 4. Enzyme kinetics of normal and chimeric glycosyltransferases

Lineweaver-Burk plots for $\alpha(1,3)$ galactosyltransferase (□) and $\alpha(1,2)$fucosyltransferase (■) to determine the apparent values for N-acetyl lactosamine. Experiments are performed in triplicate, plots shown are of mean values of enzyme activity of wild-type transferases, GT and HT, and chimeric proteins ht-GT and gt-HT in transfected COS cell extracts using phenyl-B-D Gal and N-acetyl lactosamine as acceptor substrates.

Figure 5:
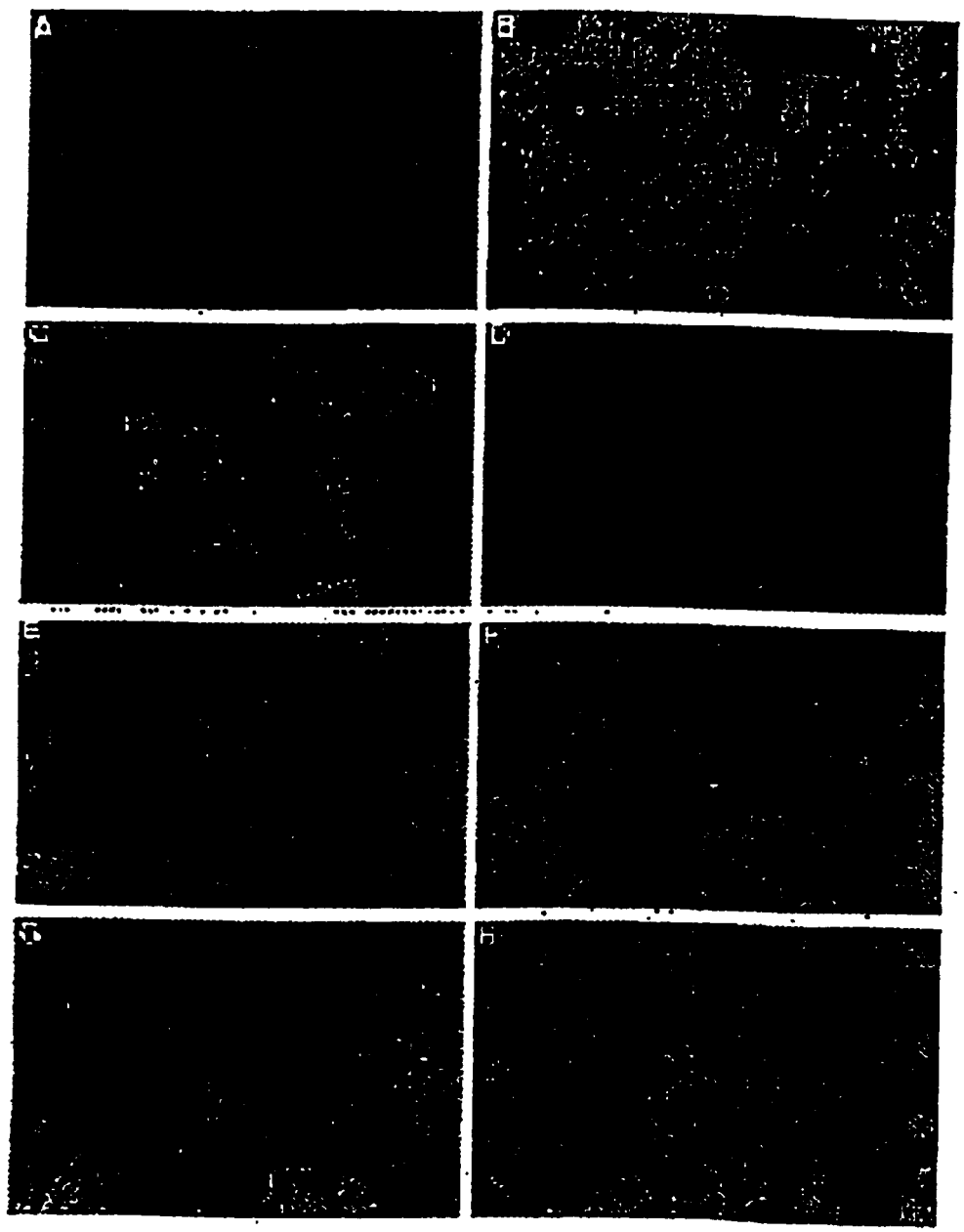

FIG. 5. Staining of cells co-transfected with chimeric transferases

Cells were co-transfected with cDNAs encoding normal transferases GT+HT (panels A, B), with chimeric transferases gt-HT+ht-GT (panels C, D), with HT+ht-GT (panels E, F) or with GT+gt-HT (panels G, H) and 48 h later were stained with FITC-labelled lectin IB4 (panels A, C, E, G) or UEAI (panels B, D, F, H).

FIG. 6 (SEQ ID No. 1) is a representation of the nucleic acid sequence and corresponding amino acid sequence of pig secretor.

FIG. 7 (SEQ ID No. 3) is a representation of the nucleic acid sequence and corresponding amino acid sequence of pig H.

Figure 8:
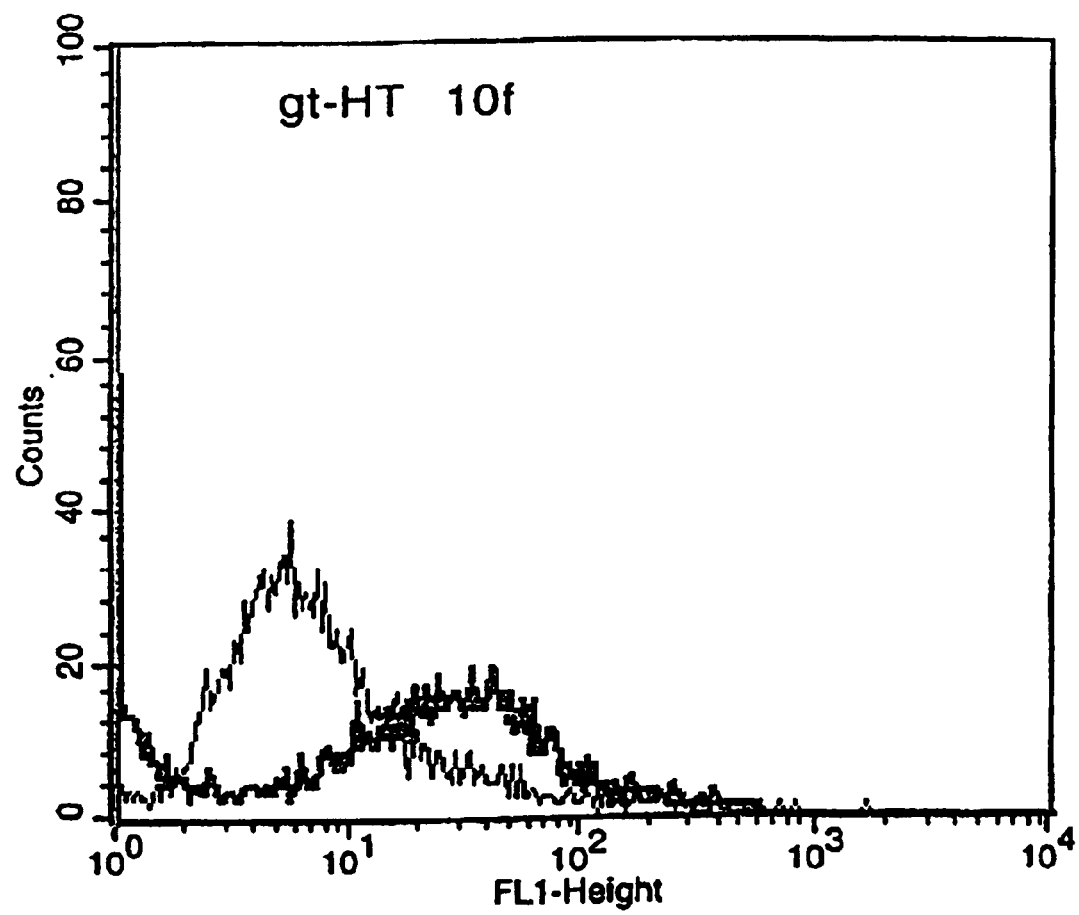

FIG. 8 Cell surface staining of pig endothelial cell line (PIEC) transfected with chimeric $\alpha(1,2)$-fucosyltransferase. Cells were transfected and clones exhibiting stable integration were stained with UFEAI lectin and visualised by fluorescence microscopy.

Figure 9:

FIG. 9 Screening of chimeric $\alpha(1,2)$-fucosyltransferase transferase in mice. Mice were injected with chimeric $\alpha(1,2)$-fucosyltransferase and the presence of the transferase was analysed by dot blots.

DESCRIPTION OF THE PREFERRED EMBODIMENT

The nucleic acid sequences encoding the catalytic domain of a glycosyltransferase may be any nucleic acid sequence such as those described in PCT/US95/07554, which is herein incorporated by reference, provided that it encodes a functional catalytic domain with the desired glycosyltransferase activity.

Preferred catalytic domains from glycosyltransferase include H transferase and secretor. Preferably these are based on human or porcine sequences.

The nucleic acid sequences encoding the localization signal of a second transglycosylase may be any nucleic acid sequence encoding a signal sequence such as signal sequences disclosed in P A Gleeson, R D Teasdale & J Bourke, Targeting of proteins to the Golgi apparatus. Glyconjugate J. (1994) 11: 381–394. Preferably the localization sis is specific for the Golgi apparatus, more preferably for that of the true Golgi. Still more preferably the localization signal is based on that of Gal transferase. Even more preferably the localization signal is based on porcine, murine or bovine sequences. Even more preferably the nucleic acid encodes a signal sequence with following amino acid sequence (in single letter code): MNVKGR (porcine) (SEQ ID NO. 11), MNVKGK (mouse) (SEQ ID NO. 12) or MVVKGK (bovine) (SEQ ID NO. 13).

Vectors for expression of the chimeric enzyme may be any suitable rector, including those disclosed in PCT/US95/07554.

The nucleic acid of the invention can be used to produce cells and organs with the desired glycosylation pattern by standard techniques, such as those disclosed in PCT/US95/07554. For example, embryos may be transfected by standard techniques such as microinjection of the nucleic acid in a linear form into the embryo (22). The embryos are then used to produce live animals, the organs of which may be subsequently used as donor organs for implantation.

Cells, tissues and organs suitable for use in the invention will generally be mammalian cells. Examples of suitable cells and tissues such as endothelial cells, hepatic cells, pancreatic cells and the like are provided in PCT/US95/07554.

The invention will now be described with reference to the following non-limiting Examples.

Abbreviations

The abbreviations used are bp, base pair(s); FITC, fluorescein isothiocyanate; GT, galactosyltransferase; H substance, $\alpha(1,2)$fucosyl lactosamine; HT, $\alpha(1,2)$ fucosyltransferase; PCR, polymerase chain reaction;

Example 1 Cytoplasmic domains of glycosyltransferases play a central role in the temporal action of enzymes Experimental Procedures

EXAMPLE 1

Plasmids—The plasmids used were prepared using standard techniques (7); pGT encodes the cDNA for the porcine $\alpha(1,3)$galactosyltransferase (23), pHT encodes the cDNA for the $\alpha(1,2)$fucosyltransferase (human) (25). Chimeric glycosyltransferase cDNAs were generated by polymerase chain reaction as follows: an 1105 bp product ht-GT was generated using primers corresponding to the 5' end of ht-GT (5'-GC<u>GGATCC</u>ATGTGGCTCCGGAGCC ATCGT-CAGGTGGTTCTGTCAATGC TGCTTG-3') (SEQ ID NO. 5) coding for nucleotides 1–24 of HT (25) followed immediately by nucleotides 68–89 of GT (8) and containing a BamH1 site (underlined) and a primer corresponding to the 3' end of ht-GT (5'-GC<u>TCTAGA</u>GCGTCAGATGTTATT TCTAACCAAATTATAC-3') (SEQ ID NO. 6) containing complementarity to nucleotides 1102–1127 of GT with an XbaI site downstream of the translational stop site (underlined); an 1110 bp product gt-HT was generated using primers corresponding to the 5' end of gt-HT (5'-GC <u>GGATCC</u>ATGAATGTCAAAGGAAGACTCTGCCTGGCCT TCCTGC-3') (SEQ ID NO. 7) coding for nucleotides 49–67 of GT followed immediately by fnucleotides 25–43 of HT and containing a BamH1 site (underlined) and a primer corresponding to the 3' end of gt-HT (5'-GC <u>TCTAGA</u>GCCTCAAGGCTTAG CCAATGTCCAGAG-3') (SEQ ID NO. 8) containing complementarity to nucleotides 1075–1099 of HT with a XbaI site downstream of the translational stop site (underlined). PCR products were restricted BamH1/Xba1, gel-purified and ligated into a BamH1/Xba1 digested pcDNA1 expression vector (Invitrogen) and resulted in two plasmids pht-GT (encoding the chimeric glycosyltransferase ht-GT) and pgt-HT (encoding the chimeric glycosyltransferase gt-HT) which were characterized by restriction mapping, Southern blotting and DNA sequencing.

Transfection and Serology—COS cells were maintained in Dubecco's modified Eagles Medium (DMEM) (Trace Biosciences Pty. Ltd., Castle Hill, NSW, Australia) and were transfected (1–10 µg DNA/5×105 cells) using DEAE-Dextrau (26); 48 h later cells were examined for cell surface expression of H substance or Gal-$\alpha(1,3)$-Gal using FITC-conjugated lectins: IB4 lectin isolated from Griffonia simplicifolia (Sigma, St. Louis, Mo.) detects Gal-$\alpha(1,3)$-Gal (27); UEAI lectin isolated from Ulex europaeus (Sigma, St. Louis, Mo.) detects H substance (28). H substance was also detected by indirect immunofluorescence using a monoclonal antibody (mAb) specific for the H substance (ASH-1952) developed at the Austin Research Institute, using FITC-conjugated goat anti-mouse IgG (Zymed Laboratories, San Francisco, Calif.) to detect mAb binding. Fluorescence was detected by microscopy.

RNA Analyses—Cytoplasmic RNA was prepared from transfected COS cells using RNAzol (Biotecx Laboratories, Houston, Tex.), and total RNA was electrophoresed in a 1% agarose gel containing formaldehyde, the gel blotted onto a nylon membrane and probed with random primed GT or HT cDNA.

Glycosyltransferase assays—Forty-eight hours after transfection, cells were washed twice with phosphate buffered saline and lysed in 1% Triton X-100/100 mM cacodylate pH 6.5/25 mM MnCl2, at 4° C. for 30 min; lysates were centrifuged and the supernatant collected and stored at −70° C. Protein concentration was determined by the Bradford method using bovine serum allumin as standard (29). Assays for HT activity (30) were performed in 25 µl containing 3 mM [GDP-$^{14}$C]fucose (specific activity 287 mCi/mmol, Amersham International), 5 mM ATP, 50 mM MPS pH 6.5, 20 mM MnCl2, using 2–10 µl of cell extract (approximately 15–20µg of protein) and a range of concentrations (7.5–75 mM) of the acceptor phenyl-B-D-galactoside (Sigma). Samples were incubated for 2 h at 37° C. and reactions terminated by the addition of ethanol and water. The amount of $^{14}$C-fucose incorporated was counted after separation from unincorporated label using Sep-Pak C18 cartridges (Waters-Millipore, Millford, Mass.). GT assays (31) were performed in a volume of 25 µl using 3 mM UDP[$^3$H]-Gal (specific activity 189 mCi/mmol, Amersham International), 5 mM ATP, 100 mM cacodylate pH 6.5, 20 mM MnCl$_2$ and various concentrations (1–10 mM) of the acceptor N-acetyl lactosamine (Sigma). Samples were incubated for 2 h at 37° C. and the reactions terminated by the addition of ethanol and water. $^3$H-Gal incorporation was counted after separation from non-incorporated UDP[$^3$H]-Gal using Dowex I anion exchange columns (BDH Ltd., Poole, UK) or Sep-Pak Accell plus QMA anion exchange cartridges (Waters-Millipore, Millford, Mass.). All assays were performed in duplicate and additional reactions were performed in the absence of added acceptor molecules, to allow for the calculation of specific incorporation of radioactivity.

Results

Figure 1:
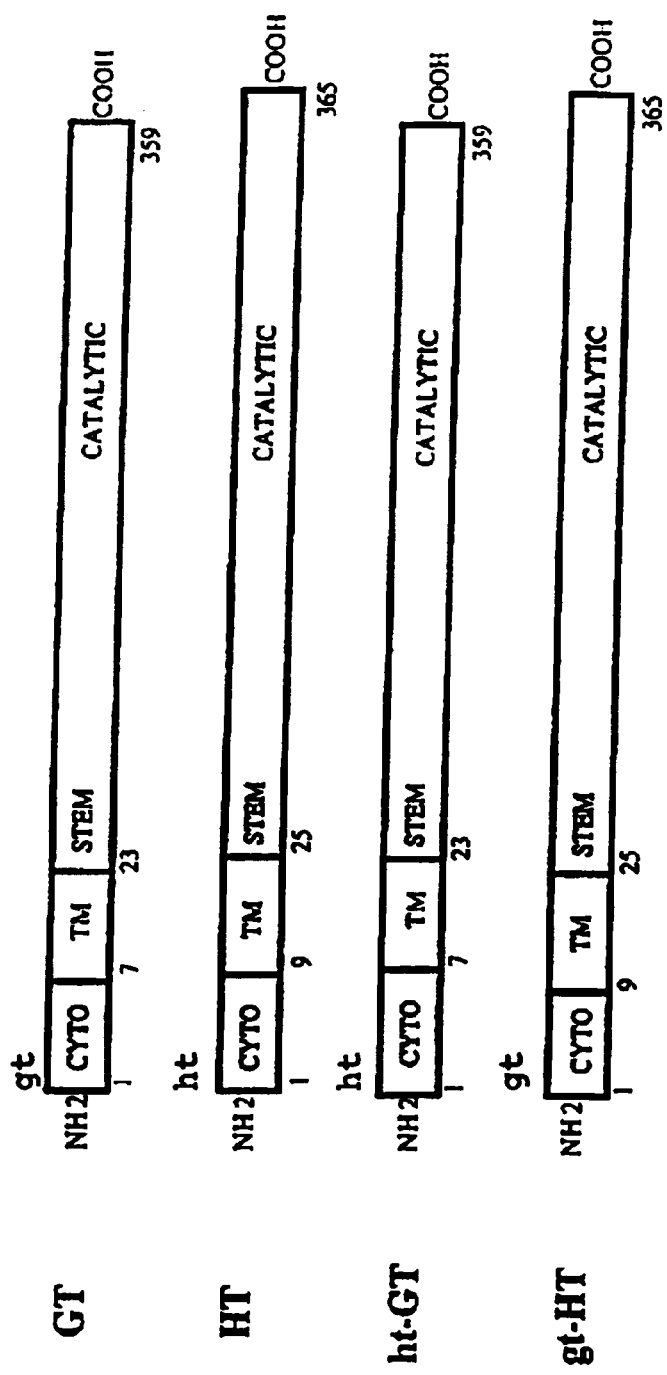
FIG. 1 Schematic diagram of normal and chimeric glycosyltransferases

Expression of chimeric $\alpha(1,3)$galactasyltransferase and $\alpha(1,2)$fucosultransferase cDNAs We had previously shown that when cDNAs encoding $\alpha(1,3)$galactosyltransferase (GT) and $\alpha(1,2)$ fucosyltransferase (HT) were transfected separately they could both function efficiently leading to expression of the appropriate carbohydrates: Gal-$\alpha(1,3)$-Gal for GT and H substance for HT (32). However when the cDNAs for GT and HT were transfected together, the HT appeared to "dominate" over the GT in that H substance expression was normal, but Gal-α(1,3)-Gal was reduced. We excluded trivial reasons for this effect and considered that the localization of the enzymes may be the reason. Thus, if the HT localization signal placed the enzyme in an earlier temporal compartment than GT, it would have "first use" of the N-acetyl lactosamine substrate. However, such a "first use" if it occurred, was not sufficient to adequately reduce GT. Two chimeric glycosyltransferases were constructed using PCR wherein the cytoplasmic tails of GT and RT were switched. The two chimeras constructed are shown in FIG. 1: ht-GT which consisted of the $NH_2$ terminal cytoplasmic tail of HT attached to the transmembrane, stem and catalytic domain of GT; and gt-HT which consisted of the $NH_2$ terminal cytoplasmic tail of GT attached to the transmembrane, stem and catalytic domains of HT. The chimeric cDNAs were subcloned into the eukaryotic expression vector pcDNAI and used in transfection experiments.

The chimeric cDNAs encoding ht-GT and gt-HT were initially evaluated for their ability to induce glycosyltransferase expression in COS cells, as measured by the surface expression of the appropriate sugar using lectins. Forty-eight hours after transfection COS cells were tested for their expression of Gal-α(1,3)-Gal or H substance (Table 1 & FIG. 2). The staining with IB4 (lectin specific for Gal-α(1,3)-Gal) in cells expressing the chimera ht-GT (30% of cells stained positive) was indistinguishable from that of the normal GT staining (30%) (Table 1 & FIG. 2). Similarly the intense cell surface fluorescence seen with UEAI staining (the lectin specific for H substance) in cells each expressing gt-HT (50%) was similar to that seen in cells expressing wild-type pHT (50%) (Table 1 & FIG. 2). Furthermore, similar levels of mRNA expression of the glycosyltransferases GT and HT and chimeric glycosyltransferases ht-GT and gt-HT were seen in Northern blots of total RNA isolated from transfected cells (FIG. 3). Thus both chimeric glycosyltransferases are efficiently expressed in COS cells and are functional indeed there was no detectable difference between the chimeric and normal glycosyltransferases.

Glycosyltransferase activity in cells transfected with chimeric cDNAs encoding ht-GT and gt-HT To determine whether switching the cytoplasmic tails of GT and HT altered the kinetics of enzyme function, we compared the enzymatic activity of the chimeric glycosyltransferases with those of the normal enzymes in COS cells after transfection of the relevant cDNAs. By making extracts from transfected COS cells and performing GT or HT enzyme assays we found that N-acetyl lactosamine was galactosylated by both GT and the chimeric enzyme ht-GT (FIG. 4. panel A) over a the 1–5 mM range of substrate concentrations. Lineweaver-Burk plots showed that both GT and ht-GT have a similar apparent Michealis-Menten constant of Km 2.6 mM for N-acetyl lactosamine (FIG. 4. panel B). Further HT, and the chimeric enzyme gt-HT were both able to fucosylate phenyl-B-D-galactoside over a range of concentrations (7.5–25 mM) (FIG. 4 panel C) with a similar Km of 2.3 mM (FIG. 4 panel D), in agreement with the reported Km of 2.4 mM for HT (25). Therefore the chimeric glycosyltransferases ht-GT and gt-HT are able to utilize N-acetyl lactosamine (ht-GT) and phenyl-B-D-galactoside (gt-HT) in the same way as the normal glycosyltransferases, thus switching the cytoplasmic domains of GT and HT does not alter the function of these glycosyltransferases and if indeed the cytoplasmic tail is the localization signal then both enzymes function as well with the GT signal as with the HT signal.

Switching Cytoplasmic Domains of GT and HT Results in a Reversal of the "Dominance" of the Glycosyltransferases The cDNAs encoding the chimeric transferases or normal transferases were simultaneously co-transfected into COS cells and after 48 h the cells were stained with either IB4 or UEA1 lectin to detect Gal-α(1,3)-Gal and H substance respectively on the cell surface (Table 1 & FIG. 5). COS cells co-transfected with cDNAs for ht-GT+gt-HT (FIG. 5 panel C) showed 30% cells staining positive with IB4 (Table 1) but no staining on cells co-transfected with cDNAs for GT+HT (3%) (FIG. 5 panel A). Furthermore staining for H substance on the surface of ht-GT+gt-H co-transfectants gave very few cells staining positive (5%) (FIG. 5 panel D) compared to the staining seen in cells co-transfected with cDNAs for the normal transferases GT+HT (50%) (FIG. 5 panel B), ie. the expression of Gal-α(1,3)-Gal now dominates over that of H. Clearly, switching the cytoplasmic tails of GT and HT led to a complete reversal in the glycosylation pattern seen with the normal transferases i.e. the cytoplasmic tail sequences dictate the pattern of carbohydrate expression observed.

That exchanging the cytoplasmic tails of GT and HT reverses the dominance of the carbohydrate epitopes points to the glycosyltransferases being relocalized within the Golgi. To address this question, experiments were performed with cDNAs encoding glycosyltransferases with the same cytoplasmic tail: COS cells transfecterases with cDNAs encoding HT+ht-GT stained strongly with both UEAI (50%) and IB4 (30%) (Table 1 & FIG. 5 panels E, F) the difference in staining reflecting differences in transfection efficiency of the cDNAs. Similarly cells transfected with cDNAs encoding GT+gt-HT also stained positive with UEAI (50%) and IB4 (30%) (Table 1 & FIG. 5 panel G, H). Thus, glycosyltransferases with the same cytoplasmic tail leads to equal cell surface expression of the carbohydrate epitopes, with no "dominance" of one glycosyltransferase over the other observed, and presumably the glycosyltransferases localized at the same site appear to compete equally for the substrate.

In COS cells the levels of transcription of the cDNAs of chimeric and normal glycosyltransferases were essentially the same (FIG. 3) and the immunofluorescence pattern of COS cells expressing the chimeric glycosyltransferases: ht-GT and gt-HT showed the typical staining pattern of the cell space Gal-α(1,3)-Gal and H substance respectively (Table 1 & FIG. 2), the pattern being indistinguishable from that of COS cells expressing normal GT and HT. Our studies showed that the Km of ht-GT for N-acetyl lactosamine was identical to the Km of GT for this substrate, similarly the Km of gt-HT for phenylBDgalactoside was approximately the same as the Km of HT for phenylbDgalactoside (FIG. 3). These findings indicate that the chimeric enzymes are functioning in a cytoplasmic tail-independent manner, such that the catalytic domains are entirely functional, and are in agreement with those of Henion et al (23), who showed that an $NH_2$ terminal truncated marmoset GT (including truncation of the cytoplasmic and transmembrane domains) maintained catalytic activity and confirmed that GT activity is indeed independent of the cytoplasmic domain sequence.

If the Golgi localization signal for GT and HT is contained entirely within the cytoplasmic domains of the enzymes, then switching the cytoplasmic tails between the two transferases should allow a reversal of the order of glycosylation. Co-transfection of COS cells with cDNA encoding the chimeric glycosyltransferases ht-GT and gt-HT caused a reversal of staining observed with the wild type glycosyltransferases (FIG. 5), demonstrating that the order of glycosylation has been altered by exchanging the cytoplasmic tails. Furthermore, co-transfection with CDNA encoding glycosyltransferases with the same cytoplasmic tails (i.e. HT+ht-GT and GT+gt-HT) gave rise to equal expression of both Gal-α(1,3)-Gal and H substance (FIG. 5). The results imply that the cytoplasmic tails of GT and HT are sufficient for the localization and retention of these two enzymes within the Golgi.

To date only twenty or so of at least one hundred predicted glycosyltransferases have been cloned and few of these have been studied with respect to their Golgi localization and retention signals (34). Studies using the elongation transferase N-acetylglucosaminyltransferase (33–37), the terminal transferases α(2,6)sialyltransferase (24–26) and β(1,4)galactosyltransferase (38–40) point to residues contained within the cytoplasmic tail, transmembrane and flanking stem regions as being critical for Golgi localization and retention. There are several examples of localization signals existing within cytoplasmic tail domains of proteins including the KDEL (SEQ ID NO: 15) and KKXX (SEQ ID NO: 16) motifs in proteins resident within the endoplasmic reticulum (41,42) the latter motif also having been identified in the cis Golgi resident protein ERGIC-53 (43) and a di-leucine containing peptide motif in the mamlose-6- phosphate receptor which directs the receptor from the trans-Golgi network to endosomes (44). These motifs are not present within the cytoplasmic tail sequences of HT or GT or in any other reported glycosyltransferase. To date a localization signal in Golgi resident glycosyltransferases has not been identified and while there is consensus that transmembrane domains are important in Golgi localization, it is apparent that this domain is not essential for the localization of all glycosyltransferases, as shown by the study of Munro (45) where replacement of the transmembrane domain of α(2,6)sialyltransferase in a hybrid protein with a poly-leucine tract resulted in normal Golgi retention. Dahdal and Colley (46) also showed that sequences in the transmembrane domain were not essential to Golgi retention. This study is the first to identify sequence requirements for the localization of α(1,2) fucosyltransferase and α(1,3) galactosyltransferase within the Golgi. It is anticipated that other glycosyltransferases will have similar localization mechanisms.

EXAMPLE 2

Use of Secretor in Construction of a Chimeric Enzyme

A construct is made using PCR and subcloning as described in Example 1, such that amino acids #1 to #6 of the pig α(1,3)-galactosyltransferase (MNVKGR) (SEQ ID NO: 14) replace amino acids #1 to #5 of the pig secretor (FIG. 6). Constructs are tested as described in Example 1.

EXAMPLE 3

Use of Pig H Transferase in Construction of a Chimeric Enzyme

A construct is made using PCR and subcloning as described in Example 1, such that amino acids #1 to #6 of the pig α(1,3)-galactosyltransferase (MNVKGR) (SEQ ID NO. 14) replace amino acids #1 to 8 of the pig H transferase (FIG. 7). Constructs are tested as described in Example 1.

EXAMPLE 4

Generation of Pig Endothelial Cells Expressing Chimeric α(1,2)Fucosyltransferase The pig endothelial cell line PIEC expressing the chimeric α1,2fucosyltransferase was produced by lipofectamine transfection of pgtHT plasmid DNA (20 μg) and pSV2NEO (2 μg) and selecting for stable integration by growing the transfected PIEC in media containing G418 (500 μg/ml; Gibco-BRL, Gaithersburg, Md.). Fourteen independant clones were examined for cell surface expression of H substance by staining with UEA-1 lectin. >95% of cells of each of these clones were found to be positive. FIG. 8 shows a typical FACS profile obtained for these clones.

EXAMPLE 5

Production of Transgenic Mice Expressing Chimeric α(1,2)Fucosyltransferase

A NruI/NotI DNA fragment, encoding the full length chimeric α1,2fucosyltransferase, was generated utilizing the Polymerase Chain Reaction and the phHT plasmid using the primers:

5' primer homologous to the 5' UTR:
5'-T<u>TCGCGA</u>ATGAATGTCAAAGGAAGACTCTG,
(SEQ ID NO. 9) in which the underlined sequence contains a unique NruI site;
3' primer homologous to the 3' UTR:
5'-G<u>GCGGCCGC</u>TCAGATGTTATTTCTAACCAAAT the underlined sequence contains a NotI site The DNA was purified on gels, electroeluted and subcloned into a NruI/NotI cut genomic H-2Kb containing vector resulting in the plasmid clone (pH-2Kb-gtHT) encoding thee chimeric α(1,2)-fucosyltransferase gene directionally cloned into exon 1 of the murine H-2Kb gene, resulting in a transcript that commences at the H-2Kb transcriptional start site, continuing through the gtHT cDNA insert. The construct was engineered such that translation would begin at the initiation condon (ATG) of the hHT cDNA and terminate at the in-phase stop codon (TGA).

DNA was prepared for microinjection by digesting pH-2Kb-hHT with XhoI And purification of the H-2Kb-hRT DNA from vector by electrophoretic separation in agarose gels, followed by extraction with chloroform, and precipitation in ethanol to decontaminate the DNA. Injections were performed into the pronuclear membrane of (C57BL/6xSJL) F1 zygotes at concentrations between 2–5 ng/ml, and the zygotes transferred to pseudopregnant (C57BL/6xSJL)F1 females.

The presence of the transgene in the live offspring was detected by dot blotting. 5 mg of genomic DNA was transferred to nylon filters and hybridized with the insert from gtHT, using a final wash at 68° C. in 0.1xSSC/1% SDS. FIG. 9 thaws the results of testing 12 live offspring, with two mice having the transgenic construct integrated into the genome. Expression of transgenic protein is examined by estimating the amount of UEAI lectin (specific for H substance) or anti-H mAb required to haemagglutinate red blood cells from transgenic mice. Hemagglutination in this assay demonstrates transgene expression.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

TABLE 1

EXPRESSION OF GAL-α(1,3)GAL AND H SUBSTANCE BY COS CELLS TRANSFECTED WITH cDNAs ENCODING NORMAL AND CHIMERIC GLYCOSYLTRANSFERASES

| COS cells transfected with cDNA encoding: | % IB4 positive cells | % UEAI positive cells |
|---|---|---|
| GT | 30 | 0 |
| HT | 0 | 50 |
| ht – GT | 30 | 0 |
| gt – HT | 3 | 50 |
| GT + HT | 3 | 50 |
| ht – GT + gt – HT | 33 | 5 |
| GT + gt – HT | 30 | 30 |
| GT + ht – GT | 30 | 0 |
| HT + ht – GT | 30 | 30 |
| HT + gt – HT | 0 | 50 |
| Mock | 0 | 0 |

Transfected COS cells were stained with FITC-labelled IB4 (lectin specific for Gal-α(1,3)Gal or UEAI (lectin specific for H substance) and positive staining cells were visualized and counted by fluorescence microscopy. Results are from at least three replicates.

References
1. Leventhal, J R et al. Complement depletion prolongs discordant cardiac xenograft survival in rodents and non-human primates. Transplant Prod. 25, 398–399 (1993).
2. Pruitt, S et al. The effect of soluble complement receptor type 1 on hyperacute rejection of porcine xenografts. Transplantation 57, 363–370 (1994).
3. Leventhal, J R et al. Removal of baboon and human antiporcine IgG and IgM natural antibodies by immuno-absorption. Transplantation 59, 294–300 (1995).
4. Brewer, R J et al. Depletion of performed natural antibody in primates for discordant xenotransplantation by continuous donor organ plasma perfusion. Transplantation Proac 25, 385–386 (1993).
5. McCurry, K R et al. Human complement regulatory proteins protect swine-to-primate cardiac xenografts from humoral injury. Nature Med. 1, 423–427 (1995).
6. Fodor, W L et al. Expression of a functional human complement inhibitor in a transgenic pig as a model for the prevention of xenogeneic hyperacute organ rejection. Proc. Natn. Acad. Sci USA 91, 11153–11157 (1994).
7. Rosengard, A M et al. Tissue expression of the human complement inhibitor decay accelerating factor in transgenic pigs. Transplantation 59, 1325–1333 (1995).
8. Sandrin, M S, Vaughan, H A, Dabkowski, P L & McKenzie, I F C. Anti-pig IgM antibodies in human serum reacts predominantly with Gal(a1,3)Gal epitopes. Prod. Natn. Acad. Sci USA 90, 11391–11395 (1993).
9. Sandrin, M S, Vaughan, H A & McKenzie, I F C. Identification of Gal(a1,3)Gal as the major epitope of pig-to-human vascularised xenografts. Transplantation Rev. 8, 134–149 (1994).
10. Sandrin, M S & McKenzie, I F C. Gal(a1,3)Gal, the major xenoantigen(s) recognised in pigs by human natural antibodies. Immunol. Rev. 141. 169–190 (1994).
11. Coopor, D K C et al. Identification of a-galactosyl and other carbohydrate epitopes that are bound by human anti-pig antibodies. Relevance to discordant xenografting in man. Transplantation Immun. 1. 198–205 (1993).
12 Cooper, D K C, Kore, E & Oriol, R Oligosacaharides and discordant xenotransplantation. Immunol. Rev. 141. 31–58 (1994).
13. Good, A H et al Identification of carbohydrate structures that bind antiporcine antibodies: Implications for discordant xenografting in humans. Transplantation Proc. 24. 559–562 (1992).
14. Galili, U., Clark, M R., Shohet, S B., Buehler, J & Macher, B A. Evolutionary relationship between the natural anti-Gal antibody and the Galal-3Gal epitope in primates. Proc. Natn. Acad. Sci USA 84. 1369–1373 (1987).
15. Galli, U., Shohet, S B., Korbin, E., stults, C L M & Macher, B A. Man, apes and Old world monkeys differ from other mammals in the expression of the a-galactosyl epitopes on nucleated cells. J. biol. Chem. 263. 17755–17762 (1988).
16. Larsen, R D et al. Isolation of a cDNA encoding a murine UDPgalactose:b-D-galetosyl-1, 4-N-acetyl-glucosaminde-1,3-galactosyltransferase: Expression cloning by gene transfer. Proc. natu. Acd. Sci. USA 86. 8227–8231d (1989).
17. Joziasse, D H., Shaper, J H., Kim D., Van den Eijuden, D H & Shaper, J H. Murine a1,3 galactosyltransferase a single gene lotus specifies four isoforms of the enzyme by alternative splicing. J. biol. Chem 267, 5534–5541 (1992).
18. Joziasse, D H, Shaper, J H, Van den Eijnden, D H, Van Tunen, A J & Shaper, N L. bovine a1,3 galactosyltransferase: Isolation and characterization of a cDNA cone. Identification of homologous sciences in human genomic DNA. J. Biol, Chem. 264. 14290–14297. (1989).
19. Sandrin, M S, Dabkowski, P I, Henning, M M, Mouhtouris, E & McKenzie, I F C. Characterization of cDNA clones for porcine a1,3 galactosyltransferase. The enzyme generating the Gal(a1, 3)Gal epitope. Xenotransplantation 1, 81–88 (1994).
20. Joziasse, D H. Shaper, J H, Jabs, F W & Shaper, N L. Characterization of an a1,3-galactosyltransferase homologue on human chromosome 12 that is organized as a processed pseudogene. J. Biol. Chem. 266. 6991–6998 (1991).
21. Larsen, R D, Riverra-Marrero, C A, Ernst, L K, Cummings, R D & Lowe, J B. Frameshift and non sense mutations in a human genomic sequence homologous to a murine UDP-Gal:b-D-Gal 1,4-D-GlcNAca1,3-galactosyl-transferase cDNA J. Biol. Chem 265. 7055–7061 (1990).
22. Kiote, C et al. Introduction of a (1,2)-fucosyltransferase and its effect on a-Gal epitopes in transgenic pig. Xenotransplantation 3:81–86.
23. Sandrin, M. S., Dabkowski, P. L., Henning, M. M., Mouhtouris, E., and McKenzie, I. F. C. (1994) Xenotransplantation 1, 81–88
24. Cohney, S., Mouhtouris, E., McKenzie, I. F. C., and Sandrin, M. S. (1996) Immunogenetics 44(1), 76–79
25. Larsen, R. D., Ernst, L. K., Nair, R. P., and Lowe, J. B. (1990) Proc. Natl. Acad. Sci. USA 87, 6674–6678
26. Sandrin, M. S., Vaughan, H. A., Dabkowski, P. L., and McKenzie, I. F. C. (1993) Proc. Natl. Acad. Sci. USA 90, 11391–11395
27. Hayes, C. E., and Goldstein, I. J. (1974) J. Biol. Chem. 6, 1904–1914
28. Matsumoto, I., and Osowa, T. (1969) Biochim. Biophys. Acta 194, 180–189
29. Bradford, M. M. (1976) Anal. Biochem. 72, 248–254
30. Rajan, V. R., Larsen, R. D., Ajmera, S., Ernst, L. K., and Lowe, J. B. (1989) J. Biol. Chem 264, 11158–11167
31. Van der Eijnden, D. H., Blanken, W. M., Winterwarp, H., and Schiphorst, W. E. C. M. (1983) Eur. J. Biochem. 134, 523–530

32. Sdri, M. S., Fodor, W. F., Mountouris, E., Osman, N., Cohney, S. C., Rollins, S. A., Guilmette, E. R., Setter, E., Squinto, S. P., and McKenzie, I. F. C. (1995) Nature Med 1, 1261–1267
33. Henion, T. R., Macher, B. A., Anaraki, F., and Galili, U. (1994) Glycobiology 4, 193–201
34. Sahacter, H. (1994) in Molecular Glycobiology (Pukuda, M., and Hindsgaul, O., eds), pp. 83–162, Oxford University Press, Oxford
35. Burke, J., Pettitt, J. M., Schachler, H., Sarkar, M., and Gleoson, P. A. (1992) J. Biol. Chem. 267, 24433–24440
36. Tang, B. L., Wong, S. H., Low, S. H., and Hong, W. (1992) J. Biol. Chem. 267, 10122
37. Nilsson, T., Pypeart, N., Hoe, M. H., Slusarewicz, P., Berger E., and Warren, G. (1993) J. Cell Biol. 120, 5-
38. Nilsson, T., Lucocq, J. M., Mackay, D., and Warren, G. (1991) EMBO J. 10, 3567–3575
39. Aoki, D., Lee, N., Yamaguchi N., Dubois, C., and Fukuda, M. N. (1992) Proc natl. Acad. Sci. USA 89, 4319–4323
40. Teasdale, R. D., D'Agostaro, G. D., and Gleeson, P. A. (1992) J. Biol. Chem. 267, 4084–4096
41. Pelham, H. R. (1990) Trends Biochem. Sci. 15, 483–486
42. Jackson, M. R., Nilsson, T., and Peterson, P. A. (1990) EMBO J. 9, 3153–3162
43. Kappeler, F., Itin, C., Schindler. R., and Hauri, H.-P. (1994) J. Biol. Chem.; 269, 6279–6281
44. Johnson, K. F., and Kornfeld, S. (1992) J. Biol. Chem. 267, 17110–17115
45. Munro, S. (1991) EMBO J. 10, 3577–3588
46. Dahdal, R. Y., and Colley, K. J. (1993) T. Biol. Chem. 268, 26310–26319

SEQUENCE LISTING

```
<160> NUMBER OF SEQ ID NOS: 16

<210> SEQ ID NO 1
<211> LENGTH: 1043
<212> TYPE: DNA
<213> ORGANISM: Sus Domesticus
<220> FEATURE:
<221> NAME/KEY: CDS
<222> LOCATION: (9)..(1031)

<400> SEQUENCE: 1 ctacagcc atg ctc agc atg cag gca tcc ttc ttc ccc acg ggt ccc        50
         Met Leu Ser Met Gln Ala Ser Phe Phe Pro Thr Gly Pro
          1               5                  10 ttc atc ctc ttt gtc ttc acg gct tcc acc ata ttt cac ctt cag cag    98
Phe Ile Leu Phe Val Phe Thr Ala Ser Thr Ile Phe His Leu Gln Gln
 15                  20                  25                  30 agg atg gtg aag att caa ccc acg tgg gag tta cag atg gtg acg cag   146
Arg Met Val Lys Ile Gln Pro Thr Trp Glu Leu Gln Met Val Thr Gln
                 35                  40                  45 gtg acc aca gag agc ccc tcg agc ccc cag ctg aag ggc atg tgg acg   194
Val Thr Thr Glu Ser Pro Ser Ser Pro Gln Leu Lys Gly Met Trp Thr
             50                  55                  60 atc aat gcc atc ggc cgc ctg ggg aac cag atg ggg gag tac gcc acc   242
Ile Asn Ala Ile Gly Arg Leu Gly Asn Gln Met Gly Glu Tyr Ala Thr
 65                  70                  75 ctg tac gcg ctg gcc agg atg aac ggg cgg ccg gcc ttc atc ccg ccc   290
Leu Tyr Ala Leu Ala Arg Met Asn Gly Arg Pro Ala Phe Ile Pro Pro
 80                  85                  90 gag atg cac agc acg ctg gcc ccc atc ttc agg atc acc ctc ccg gtc   338
Glu Met His Ser Thr Leu Ala Pro Ile Phe Arg Ile Thr Leu Pro Val
 95                 100                 105                 110 ctg cac gcc agc acg gcc cgc agg atc ccc tgg cag aac tac cac ctg   386
Leu His Ala Ser Thr Ala Arg Arg Ile Pro Trp Gln Asn Tyr His Leu
                115                 120                 125 aac gac tgg atg gag gag cgg tac cgc cac atc ccg ggg gag tac gtg   434
Asn Asp Trp Met Glu Glu Arg Tyr Arg His Ile Pro Gly Glu Tyr Val
            130                 135                 140 cgc ctc acg ggc tac ccc tgc tcc tgg acc ttc tac cac cac ctg cgc   482
Arg Leu Thr Gly Tyr Pro Cys Ser Trp Thr Phe Tyr His His Leu Arg
            145                 150                 155 acc gag atc ctc cgg gag ttc acc ctg cat aac cac gtg cgc gag gag   530
Thr Glu Ile Leu Arg Glu Phe Thr Leu His Asn His Val Arg Glu Glu
```

```
                    160                 165                 170
gcc cag gat ttc ctg cgg ggt ctg cgg gtg aac ggg agc cga ccg agt    578
Ala Gln Asp Phe Leu Arg Gly Leu Arg Val Asn Gly Ser Arg Pro Ser
175                 180                 185                 190 acc tac gtg ggg gtg cac gtg cgc cgg ggg gac tac gtg cac gtg atg    626
Thr Tyr Val Gly Val His Val Arg Arg Gly Asp Tyr Val His Val Met
                195                 200                 205 ccc aac gtg tgg aag ggc gtg gtg gcc gac cgg cgg tac ctg gag cag    674
Pro Asn Val Trp Lys Gly Val Val Ala Asp Arg Arg Tyr Leu Glu Gln
            210                 215                 220 gcc ctg gac tgg ttc cgg gct cgc tac cgc tcc ccc gtc ttt gtg gtc    722
Ala Leu Asp Trp Phe Arg Ala Arg Tyr Arg Ser Pro Val Phe Val Val
        225                 230                 235 tcc agc aac ggc atg gcc tgg tgt cgg gaa aac atc aat gcc tcg cgc    770
Ser Ser Asn Gly Met Ala Trp Cys Arg Glu Asn Ile Asn Ala Ser Arg
    240                 245                 250 ggc gat gtg gtg ttt gcc ggc aat ggc atc gag ggc tcc ccc gcc aaa    818
Gly Asp Val Val Phe Ala Gly Asn Gly Ile Glu Gly Ser Pro Ala Lys
255                 260                 265                 270 gac ttc gcg ctg ctc acg cag tgt aac cac act gtc atg acc att ggc    866
Asp Phe Ala Leu Leu Thr Gln Cys Asn His Thr Val Met Thr Ile Gly
                275                 280                 285 acg ttc ggg atc tgg gcc gcc tac ctt gct ggt gga gag acc atc tac    914
Thr Phe Gly Ile Trp Ala Ala Tyr Leu Ala Gly Gly Glu Thr Ile Tyr
            290                 295                 300 ctg gcc aat tac acg ctc ccg gac tct ccc ttc ctc aaa ctc ttt aag    962
Leu Ala Asn Tyr Thr Leu Pro Asp Ser Pro Phe Leu Lys Leu Phe Lys
        305                 310                 315 ccc gag gca gcc ttc ctg ccc gag tgg att ggg atc gag gca gac ctg    1010
Pro Glu Ala Ala Phe Leu Pro Glu Trp Ile Gly Ile Glu Ala Asp Leu
    320                 325                 330 tcc cca ctc ctt aag cac tga tgtcggctgt cc                          1043
Ser Pro Leu Leu Lys His
335                 340

<210> SEQ ID NO 2
<211> LENGTH: 340
<212> TYPE: PRT
<213> ORGANISM: Sus Domesticus

<400> SEQUENCE: 2

Met Leu Ser Met Gln Ala Ser Phe Phe Pro Thr Gly Pro Phe Ile
1               5                   10                  15

Leu Phe Val Phe Thr Ala Ser Thr Ile Phe His Leu Gln Gln Arg Met
                20                  25                  30

Val Lys Ile Gln Pro Thr Trp Glu Leu Gln Met Val Thr Gln Val Thr
            35                  40                  45

Thr Glu Ser Pro Ser Ser Pro Gln Leu Lys Gly Met Trp Thr Ile Asn
    50                  55                  60

Ala Ile Gly Arg Leu Gly Asn Gln Met Gly Glu Tyr Ala Thr Leu Tyr
65              70                  75                  80

Ala Leu Ala Arg Met Asn Gly Arg Pro Ala Phe Ile Pro Pro Glu Met
                85                  90                  95

His Ser Thr Leu Ala Pro Ile Phe Arg Ile Thr Leu Pro Val Leu His
                100                 105                 110

Ala Ser Thr Ala Arg Arg Ile Pro Trp Gln Asn Tyr His Leu Asn Asp
            115                 120                 125

Trp Met Glu Glu Arg Tyr Arg His Ile Pro Gly Glu Tyr Val Arg Leu
```

```
                130              135              140
Thr Gly Tyr Pro Cys Ser Trp Thr Phe Tyr His His Leu Arg Thr Glu
145                 150                 155                 160

Ile Leu Arg Glu Phe Thr Leu His Asn His Val Arg Glu Glu Ala Gln
                165                 170                 175

Asp Phe Leu Arg Gly Leu Arg Val Asn Gly Ser Arg Pro Ser Thr Tyr
                180                 185                 190

Val Gly Val His Val Arg Arg Gly Asp Tyr Val His Val Met Pro Asn
                195                 200                 205

Val Trp Lys Gly Val Val Ala Asp Arg Arg Tyr Leu Glu Gln Ala Leu
    210                 215                 220

Asp Trp Phe Arg Ala Arg Tyr Arg Ser Pro Val Phe Val Ser Ser
225                 230                 235                 240

Asn Gly Met Ala Trp Cys Arg Glu Asn Ile Asn Ala Ser Arg Gly Asp
                245                 250                 255

Val Val Phe Ala Gly Asn Gly Ile Glu Gly Ser Pro Ala Lys Asp Phe
                260                 265                 270

Ala Leu Leu Thr Gln Cys Asn His Thr Val Met Thr Ile Gly Thr Phe
                275                 280                 285

Gly Ile Trp Ala Ala Tyr Leu Ala Gly Gly Glu Thr Ile Tyr Leu Ala
    290                 295                 300

Asn Tyr Thr Leu Pro Asp Ser Pro Phe Leu Lys Leu Phe Lys Pro Glu
305                 310                 315                 320

Ala Ala Phe Leu Pro Glu Trp Ile Gly Ile Glu Ala Asp Leu Ser Pro
                325                 330                 335

Leu Leu Lys His
            340

<210> SEQ ID NO 3
<211> LENGTH: 1098
<212> TYPE: DNA
<213> ORGANISM: Sus Domesticus
<220> FEATURE:
<221> NAME/KEY: CDS
<222> LOCATION: (1)..(1098)

<400> SEQUENCE: 3 atg tgg gtc ccc agc cgc cgc cac ctc tgt ctg acc ttc ctg cta gtc     48
Met Trp Val Pro Ser Arg Arg His Leu Cys Leu Thr Phe Leu Leu Val
  1               5                  10                  15 tgt gtt tta gca gca att ttc ttc ctg aac gtc tat caa gac ctc ttt     96
Cys Val Leu Ala Ala Ile Phe Phe Leu Asn Val Tyr Gln Asp Leu Phe
                 20                  25                  30 tac agt ggc tta gac ctg ctg gcc ctg tgt cca gac cat aac gtg gta    144
Tyr Ser Gly Leu Asp Leu Leu Ala Leu Cys Pro Asp His Asn Val Val
             35                  40                  45 tca tct ccc gtg gcc ata ttc tgc ctg gcg ggc acg ccg gta cac ccc    192
Ser Ser Pro Val Ala Ile Phe Cys Leu Ala Gly Thr Pro Val His Pro
         50                  55                  60 aac gcc tcc gat tcc tgt ccc aag cat cct gcc tcc ttt tcc ggg acc    240
Asn Ala Ser Asp Ser Cys Pro Lys His Pro Ala Ser Phe Ser Gly Thr
 65                  70                  75                  80 tgg act att tac ccg gat ggc cgg ttt ggg aac cag atg gga cag tat    288
Trp Thr Ile Tyr Pro Asp Gly Arg Phe Gly Asn Gln Met Gly Gln Tyr
                 85                  90                  95 gcc acg ctg ctg gcc ctg gcg cag ctc aac ggc cgc cag gcc ttc atc    336
Ala Thr Leu Leu Ala Leu Ala Gln Leu Asn Gly Arg Gln Ala Phe Ile
                100                 105                 110
```

```
cag cct gcc atg cac gcc gtc ctg gcc ccc gtg ttc cgc atc acg ctg    384
Gln Pro Ala Met His Ala Val Leu Ala Pro Val Phe Arg Ile Thr Leu
    115                 120                 125 cct gtc ctg gcg ccc gag gta gac agg cac gct cct tgg cgg gag ctg    432
Pro Val Leu Ala Pro Glu Val Asp Arg His Ala Pro Trp Arg Glu Leu
130                 135                 140 gag ctt cac gac tgg atg tcc gag gat tat gcc cac tta aag gag ccc    480
Glu Leu His Asp Trp Met Ser Glu Asp Tyr Ala His Leu Lys Glu Pro
145                 150                 155                 160 tgg ctg aag ctc acc ggc ttc ccc tgc tcc tgg acc ttc ttc cac cac    528
Trp Leu Lys Leu Thr Gly Phe Pro Cys Ser Trp Thr Phe Phe His His
                165                 170                 175 ctc cgg gag cag atc cgc agc gag ttc acc ctg cac gac cac ctt cgg    576
Leu Arg Glu Gln Ile Arg Ser Glu Phe Thr Leu His Asp His Leu Arg
            180                 185                 190 caa gag gcc cag ggg gta ctg agt cag ttc cgt cta ccc cgc aca ggg    624
Gln Glu Ala Gln Gly Val Leu Ser Gln Phe Arg Leu Pro Arg Thr Gly
        195                 200                 205 gac cgc ccc agc acc ttc gtg ggg gtc cac gtg cgc cgc ggg gac tat    672
Asp Arg Pro Ser Thr Phe Val Gly Val His Val Arg Arg Gly Asp Tyr
    210                 215                 220 ctg cgt gtg atg ccc aag cgc tgg aag ggg gtg gtg ggt gac ggc gct    720
Leu Arg Val Met Pro Lys Arg Trp Lys Gly Val Val Gly Asp Gly Ala
225                 230                 235                 240 tac ctc cag cag gct atg gac tgg ttc cgg gcc cga tac gaa gcc ccc    768
Tyr Leu Gln Gln Ala Met Asp Trp Phe Arg Ala Arg Tyr Glu Ala Pro
                245                 250                 255 gtc ttt gtg gtc acc agc aac ggc atg gag tgg tgc cgg aag aac atc    816
Val Phe Val Val Thr Ser Asn Gly Met Glu Trp Cys Arg Lys Asn Ile
            260                 265                 270 gac acc tcc cgg ggg gac gtg atc ttt gct ggc gat ggg cgg gag gcc    864
Asp Thr Ser Arg Gly Asp Val Ile Phe Ala Gly Asp Gly Arg Glu Ala
        275                 280                 285 gcg ccc gcc agg gac ttt gcg ctg ctg gtg cag tgc aac cac acc atc    912
Ala Pro Ala Arg Asp Phe Ala Leu Leu Val Gln Cys Asn His Thr Ile
    290                 295                 300 atg acc att ggc acc ttc ggc ttc tgg gcc gcc tac ctg gct ggt gga    960
Met Thr Ile Gly Thr Phe Gly Phe Trp Ala Ala Tyr Leu Ala Gly Gly
305                 310                 315                 320 gat acc atc tac ttg gct aac ttc acc ctg ccc act tcc agc ttc ctg   1008
Asp Thr Ile Tyr Leu Ala Asn Phe Thr Leu Pro Thr Ser Ser Phe Leu
                325                 330                 335 aag atc ttt aaa ccc gag gct gcc ttc ctg ccc gag tgg gtg ggc att   1056
Lys Ile Phe Lys Pro Glu Ala Ala Phe Leu Pro Glu Trp Val Gly Ile
            340                 345                 350 aat gca gac ttg tct cca ctc cag atg ttg gct ggg cct tga            1098
Asn Ala Asp Leu Ser Pro Leu Gln Met Leu Ala Gly Pro
        355                 360                 365

<210> SEQ ID NO 4
<211> LENGTH: 365
<212> TYPE: PRT
<213> ORGANISM: Sus Domesticus

<400> SEQUENCE: 4

Met Trp Val Pro Ser Arg Arg His Leu Cys Leu Thr Phe Leu Leu Val
1               5                   10                  15

Cys Val Leu Ala Ala Ile Phe Phe Leu Asn Val Tyr Gln Asp Leu Phe
            20                  25                  30
```

```
Tyr Ser Gly Leu Asp Leu Leu Ala Leu Cys Pro Asp His Asn Val Val
         35                  40                  45

Ser Ser Pro Val Ala Ile Phe Cys Leu Ala Gly Thr Pro Val His Pro
     50                  55                  60

Asn Ala Ser Asp Ser Cys Pro Lys His Pro Ala Ser Phe Ser Gly Thr
 65                  70                  75                  80

Trp Thr Ile Tyr Pro Asp Gly Arg Phe Gly Asn Gln Met Gly Gln Tyr
                 85                  90                  95

Ala Thr Leu Leu Ala Leu Ala Gln Leu Asn Gly Arg Gln Ala Phe Ile
             100                 105                 110

Gln Pro Ala Met His Ala Val Leu Ala Pro Val Phe Arg Ile Thr Leu
             115                 120                 125

Pro Val Leu Ala Pro Glu Val Asp Arg His Ala Pro Trp Arg Glu Leu
         130                 135                 140

Glu Leu His Asp Trp Met Ser Glu Asp Tyr Ala His Leu Lys Glu Pro
145                 150                 155                 160

Trp Leu Lys Leu Thr Gly Phe Pro Cys Ser Trp Thr Phe Phe His His
                 165                 170                 175

Leu Arg Glu Gln Ile Arg Ser Glu Phe Thr Leu His Asp His Leu Arg
             180                 185                 190

Gln Glu Ala Gln Gly Val Leu Ser Gln Phe Arg Leu Pro Arg Thr Gly
             195                 200                 205

Asp Arg Pro Ser Thr Phe Val Gly Val His Val Arg Arg Gly Asp Tyr
         210                 215                 220

Leu Arg Val Met Pro Lys Arg Trp Lys Gly Val Val Gly Asp Gly Ala
225                 230                 235                 240

Tyr Leu Gln Gln Ala Met Asp Trp Phe Arg Ala Arg Tyr Glu Ala Pro
                 245                 250                 255

Val Phe Val Val Thr Ser Asn Gly Met Glu Trp Cys Arg Lys Asn Ile
             260                 265                 270

Asp Thr Ser Arg Gly Asp Val Ile Phe Ala Gly Asp Gly Arg Glu Ala
             275                 280                 285

Ala Pro Ala Arg Asp Phe Ala Leu Leu Val Gln Cys Asn His Thr Ile
         290                 295                 300

Met Thr Ile Gly Thr Phe Gly Phe Trp Ala Ala Tyr Leu Ala Gly Gly
305                 310                 315                 320

Asp Thr Ile Tyr Leu Ala Asn Phe Thr Leu Pro Thr Ser Ser Phe Leu
                 325                 330                 335

Lys Ile Phe Lys Pro Glu Ala Ala Phe Leu Pro Glu Trp Val Gly Ile
             340                 345                 350

Asn Ala Asp Leu Ser Pro Leu Gln Met Leu Ala Gly Pro
             355                 360                 365

<210> SEQ ID NO 5
<211> LENGTH: 54
<212> TYPE: DNA
<213> ORGANISM: Artificial Sequence
<220> FEATURE:
<223> OTHER INFORMATION: Description of Artificial Sequence: Chimeric,
      Homo Sapiens and Sus Domesticus

<400> SEQUENCE: 5
gcggatccat gtggctccgg agccatcgtc aggtggttct gtcaatgctg cttg        54

<210> SEQ ID NO 6
<211> LENGTH: 39
<212> TYPE: DNA
```

```
<213> ORGANISM: Artificial Sequence
<220> FEATURE:
<223> OTHER INFORMATION: Description of Artificial Sequence: Chimeric,
      Homo Sapiens and Sus Domesticus

<400> SEQUENCE: 6
gctctagagc gtcagatgtt atttctaacc aaattatac                    39

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Chimeric,
      Homo Sapiens and Sus Domesticus

<400> SEQUENCE: 7
gcggatccat gaatgtcaaa ggaagactct gcctggcctt cctgc             45

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Chimeric,
      Homo Sapiens and Sus Domesticus

<400> SEQUENCE: 8
gctctagagc ctcaaggctt agccaatgtc cagag                        35

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Chimeric,
      Homo Sapiens and Sus Domesticus

<400> SEQUENCE: 9
ttcgcgaatg aatgtcaaag gaagactctg                              30

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Chimeric,
      Homo Sapiens and Sus Domesticus

<400> SEQUENCE: 10
ggcggccgct cagatgttat ttctaaccaa at                           32

<210> SEQ ID NO 11
<211> LENGTH: 6
<212> TYPE: PRT
<213> ORGANISM: Sus scrofa

<400> SEQUENCE: 11

Met Asn Val Lys Gly Arg
 1               5

<210> SEQ ID NO 12
<211> LENGTH: 6
<212> TYPE: PRT
<213> ORGANISM: Mus musculus

<400> SEQUENCE: 12
```

```
Met Asn Val Lys Gly Lys
  1               5

<210> SEQ ID NO 13
<211> LENGTH: 6
<212> TYPE: PRT
<213> ORGANISM: Unknown Organism
<220> FEATURE:
<223> OTHER INFORMATION: Description of Unknown Organism:  Bovine

<400> SEQUENCE: 13

Met Val Val Lys Gly Lys
  1               5

<210> SEQ ID NO 14
<211> LENGTH: 6
<212> TYPE: PRT
<213> ORGANISM: Sus scrofa

<400> SEQUENCE: 14

Met Asn Val Lys Gly Arg
  1               5

<210> SEQ ID NO 15
<211> LENGTH: 4
<212> TYPE: PRT
<213> ORGANISM: Unknown Organism
<220> FEATURE:
<223> OTHER INFORMATION: Description of Unknown Organism:  Motif

<400> SEQUENCE: 15

Lys Asp Glu Leu
  1

<210> SEQ ID NO 16
<211> LENGTH: 4
<212> TYPE: PRT
<213> ORGANISM: Unknown Organism
<220> FEATURE:
<223> OTHER INFORMATION: Description of Unknown Organism:  Motif
<220> FEATURE:
<221> NAME/KEY: UNSURE
<222> LOCATION: (3)..(4)
<223> OTHER INFORMATION: Xaa is any amino acid

<400> SEQUENCE: 16

Lys Lys Xaa Xaa
  1
```

What is claimed is:

1. A polynucleotide encoding a chimeric enzyme comprising:
   a) a glycosyltransferase localization signal directing localization of the chimeric enzyme to the Golgi of a cell; and
   b) a catalytic domain of a fucosyl transferase that competes with galactosytransferase for substrate.

2. The polynucleotide of claim 1, wherein the fucosyl transferase is H-transferase or secretor-type alpha-1,2 fucosyl transferase.

3. The polynucleotide of claim 1, wherein the glycosyltransferase localization signal comprises a cytoplasmic domain of a glycosyltransferase.

4. The polynucleotide of claim 1, wherein the localization signal is (SEQ. ID. No. 11), MNVKGK (SEQ. ID. No. 12), or MVVKGK (SEQ. ID. No. 13).

5. A vector comprising the polynucleotide of claim 1.

6. The vector of claim 5, wherein the fucosyl transferase is H-transferase or secretor-type alpha-1,2 fucosyl transferase.

7. A method for reducing hyperacute rejection of transplanted porcine cells comprising transforming the cells with the polynucleotide of claim 1 prior to transplantation, wherein expression of the polynucleotide results in less gal-alpha-(1,3)-gal present on the cells.

8. A polynucleotide encoding a chimeric enzyme comprising:
   a) a localization signal of an alpha-1,3 galactosyl transferase enzyme;
   b) a catalytic domain of a fucosyl transferase that competes with the galactosyltransferase for substrate.

9. The polynucleotide of claim 8, wherein the fucosyl transferase is H-transferase or secretor-type alpha-1,2 fucosyl transferase.

10. The polynucleotide of claim 8, wherein the localization signal comprises a cytoplasmic domain of a glycosyltransferase.

11. The polynucleotide of claim 8, wherein the localization signal is MNVKGR (SEQ. ID. No. 11). MNVKGK (SEQ. ID. No. 12), or MVVKGK (SEQ. ID. No. 13).

12. A vector comprising the polynucleotide of claim 8.

13. The vector of claim 12, wherein the fucosyl transferase is H-transferase or secretor-type alpha-1,2 fucosyl transferase.

14. A method for reducing hyperacute rejection of transplanted porcine cells comprising transforming the cells with the polynucleotide of claim 8, prior to transplantation, wherein expression of the chimeric of the polynucleotide results in less gal-alpha-(1,3)-gal present on the cells.

15. A method for reducing an amount of gal-alpha-(1,3)-gal present on cells comprising:
    a) transducing the cells with a polynucleotide encoding chimeric enzyme, said chimeric enzyme comprising:
        i) a glycosyltransferase localization signal directing localization of the chimeric enzyme to the Golgi; and
        ii) a catalytic domain of a fucosyl transferase that competes with galactosytransferase for substrate;
    b) expressing the polynucleotide in the cells such that the chimeric enzyme is produced, wherein activity of the chimeric enzyme in the cells reduces the amount of gal-alpha-(1,3)-gal present on the cells by competing with galactosyl transferase for substrate, resulting in less substrate being converted into a gal-alpha-(1,3)-gal than in the absence of said chimeric enzyme.

16. The method of claim 15, wherein the fucosyl transferase is H-transferase or secretor-type alpha-1,2 fucosyl transferase.

17. A method of claim 15, wherein said transforming is ex vivo.

18. A method for reducing an amount of gal-alpha-(1,3)-gal present on cells comprising:
    a) transducing the cells with a polynucleotide encoding a chimeric enzyme, said chimeric enzyme comprising:
        i) a localization signal of an alpha-1,3 galactosyl transferase enzyme; and
        ii) a catalytic domain of a fucosyl transferase that competes with galactosy transferase for substrate;
    expressing the polynucleotide in the cells such that the chimeric enzyme is produced, wherein activity of the chimeric enzyme in the cells reduces the amount of gal-alpha-(1,3)-gal present on the cells by competing with galactosyl transferase for substrate, resulting in less substrate home converted into gal-alpha-(1,3)-gal than in the absence of said chimeric enzyme.

19. The method of claim 18, wherein the fucosyl transferase is H-transferase or secretor-type alpha-1,2 fucosyl transferase.

20. A method of claim 18, wherein said transforming is ex vivo.

* * * * *